US012013390B2

(12) United States Patent
Xia et al.

(10) Patent No.: US 12,013,390 B2
(45) Date of Patent: Jun. 18, 2024

(54) EBIV NUCLEIC ACID COMPOSITION AND APPLICATION THEREOF

(71) Applicant: Wuhan Institute of Virology, Chinese Academy of Sciences, Wuhan (CN)

(72) Inventors: Han Xia, Wuhan (CN); Zhiming Yuan, Wuhan (CN); Nanjie Ren, Wuhan (CN); Fei Wang, Wuhan (CN); Guilin Zhang, Wuhan (CN)

(73) Assignee: Wuhan Institute of Virology, Chinese Academy of Sciences, Wuhan (CN)

( * ) Notice: Subject to any disclaimer, the term of this patent is extended or adjusted under 35 U.S.C. 154(b) by 0 days.

(21) Appl. No.: 18/312,072

(22) Filed: May 4, 2023

(65) Prior Publication Data

US 2023/0366877 A1 Nov. 16, 2023

(30) Foreign Application Priority Data

Mar. 14, 2022 (CN) .......................... 202210249414.2

(51) Int. Cl.
| | |
|---|---|
| *C12N 15/86* | (2006.01) |
| *C12N 7/00* | (2006.01) |
| *C12N 7/01* | (2006.01) |
| *G01N 33/50* | (2006.01) |
| *G01N 33/58* | (2006.01) |

(52) U.S. Cl.
CPC ........... *G01N 33/5091* (2013.01); *C12N 7/00* (2013.01); *C12N 15/86* (2013.01); *C12N 2760/12021* (2013.01); *C12N 2760/12043* (2013.01); *C12N 2760/12052* (2013.01); *G01N 2333/175* (2013.01)

(58) Field of Classification Search
CPC .......... C12N 15/86; C12N 2760/12021; C12N 2760/12043; C12N 7/00; G01N 2333/175
See application file for complete search history.

(56) References Cited

FOREIGN PATENT DOCUMENTS

| CN | 110195093 A | 9/2019 |
|---|---|---|
| CN | 110484517 A | 11/2019 |

OTHER PUBLICATIONS

Title of the Item: Genome Announcements Publication Date: Jun. 19, 2014 Name of the Author: Ran Liu et al. Article Title: Genome Sequence of Abbey Lake Virus, a Novel Orthobunyavirus Isolated from China pp. 1.

*Primary Examiner* — Barry A Chestnut
(74) *Attorney, Agent, or Firm* — Nitin Kaushik

(57) ABSTRACT

The present application discloses a nucleic acid composition for expressing recombinant EBIV-related genes and proteins and the use thereof. The nucleic acid composition includes a nucleic acid molecule having sequences shown in SEQ ID NO. 14, 15, 16, and 17. In the present application, a recombinant EBIV is also constructed with this nucleic acid composition. The virus not only has broad-spectrum infectivity to mammalian and mosquito cells, can be stably passaged, but also has green fluorescence, which can provide a research foundation for in vitro and in vivo virus tracing, virus detection, antiviral drugs, vaccine screening, with significant application prospects.

5 Claims, 7 Drawing Sheets
Specification includes a Sequence Listing.

FIG. 1

FIG. 2

EBIV NUCLEIC ACID COMPOSITION AND APPLICATION THEREOF

CROSS-REFERENCE TO RELATED APPLICATIONS

The application claims priority to Chinese patent application No. 202210249414.2, filed on Mar. 14, 2022, the entire contents of which are incorporated herein by reference.

SEQUENCE LISTING

This application contains a "Sequence Listing" that has been submitted electronically as an XML file named "SEQUENCE_LISTING_WI_US23_6596_P.XML". The XML file, created on Jan. 24, 2024, is 52,503 bytes in size. The material in the XML file is hereby incorporated by reference in its entirety.

TECHNICAL FIELD

The present application relates to the technical field of EBIV, and in particular to an EBIV nucleic acid composition and the application thereof.

BACKGROUND

Ebinur Lake virus (EBIV), is a new member of Bunyamwera serogroup, belonging to the family Panbunyaviridae and the genus *Orthobunyavirus*. It was first isolated from *Culex modestus* in the Ebinur Lake region of Xinjiang, China in 2014. The virus is spherical in particle, membrane-coated, and the genome is composed of three independent single-stranded RNA fragments, L, M, and S. Previous studies found that mice were highly susceptible to EBIV and even extremely low doses of virus (1 plaque forming unit) can cause death in mice. Viruses were detected in the peripheral tissues and central nervous system of the infected mice, and obviously histopathologic changes were observed in the liver, spleen, thymus, and brain. Moreover, cytokine levels in the serum, spleen, and brain of mice are significantly altered by EBIV infection. Alanine aminotransferase, lactate dehydrogenase, and creatine kinase were found to be significantly higher in infected mice compared to uninfected mice, according to an analysis of blood components. Infected mice also had lower levels of white blood cells and blood platelets. It is noteworthy that the seroepidemiological survey of people around the Ebinur Lake indicated the presence of IgM, IgG, and neutralizing antibodies of EBIV in the population, suggesting that the virus has potential pathogenic and infectious risks for humans. The reverse genetics system has been used to obtain recombinant viruses, which can be further used to study viral replication, invasion, gene function, drug screening, and vaccine development. However, the use of a reverse genetics system to construct recombinant EBIV has not been reported, which hinders the further study of new mosquito-borne EBIV.

SUMMARY

In view of this, the purpose of the present application is to develop a recombinant EBIV and a method for constructing the same, so as to make up the blank of the functional study on the related gene sequences of the virus in the prior art, and to provide a basis for further exploring the pathogenicity, transmission mechanism of the virus, drug screening and vaccine development.

In a first aspect, an embodiment of the present application discloses a nucleic acid sequence combination for expressing a recombinant EBIV-related protein, comprising: an EBIV L segment, the nucleotide sequence of which is as shown in SEQ ID NO. 14; an EBIV M segment, the nucleotide sequence of which is as shown in SEQ ID NO. 15; an EBIV S segment, the nucleotide sequence of which is as shown in SEQ ID NO. 16; and a gene fragment of a green fluorescent protein, the nucleotide sequence of which is as shown in SEQ ID NO. 17.

In a second aspect, an embodiment of the present application discloses a plasmid composition comprising a recombinant plasmid constructed with the nucleotide sequences shown in SEQ ID NO. 14, 15, 16, and 17, respectively, for use in the construction of wild-type or recombinant EBIV. The term "wild-type EBIV" refers to the EBIV screened and isolated in the natural environment, and the term "recombinant EBIV" refers to the EBIV strain capable of expressing not only the conventional genetic characteristics of the EBIV, but also over-expressing/deleting certain genes or expressing certain tag genes obtained by using reverse genetics means to rescue the wild-type EBIV, or carrying out gene modification, gene marking and gene recombination on the wild-type EBIV.

In a third aspect, an embodiment of the present application discloses a set of primers for the nucleic acid composition of the first aspect, comprising: a primer pair for amplifying the nucleic acid sequence as shown in SEQ ID NO. 14, as shown in SEQ ID NO. 1 and 2; a primer pair for amplifying the nucleic acid sequence as shown in SEQ ID NO. 15, as shown in SEQ ID NO. 3 and 4; and a primer pair for amplifying the nucleic acid sequence as shown in SEQ ID NO. 16, as shown in SEQ ID NO. 5 and 6;

In a fourth aspect, an embodiment of the present application discloses a kit for amplifying the nucleic acid composition of the first aspect, comprising the set of primers of the third aspect.

In a fifth aspect, an embodiment of the present application discloses a recombinant EBIV strain carrying the gene sequences as shown in SEQ ID NO. 14, 15, 16, and 17, which was deposited at the China Center for Type Culture Collection on Jan. 25, 2022, with the deposit address of Wuhan University, Wuhan, China (address of No. 299, Bayi Road, Wuhan City, Hubei Province), and the Deposit Number of CCTCC NO. V202204.

In a sixth aspect, an embodiment of the present application discloses a recombinant host bacterium carrying the nucleic acid sequences shown in SEQ ID NO. 14, 15, 16, and 17.

In a seventh aspect, an embodiment of the present application discloses a method for preparing a recombinant EBIV strain, the method comprising the steps of amplifying the nucleic acid composition of the first aspect using the set of primers and the kit of the third and fourth aspects; ligating the gene sequence with a vector plasmid to obtain the recombinant plasmid of the second aspect; obtaining a positive clonal culture of the recombinant host bacterium carrying the recombinant plasmid of the sixth aspect; obtaining a plurality of the recombinant plasmids from the positive clone culture; transfecting the recombinant plasmid into host cells and culturing same; harvesting the transfected culture containing the recombinant EBIV strain.

In an eighth aspect, an embodiment of the present application discloses the use of the nucleic acid composition of the first aspect, wherein the use includes at least one of the preparation of a recombinant EBIV, expression of a protein associated with the recombinant EBIV, screening for drugs that antagonize EBIV, in vitro tracing of a recombinant EBIV, preparation of a vaccine against EBIV, and preparation of a product associated with detection of EBIV Compared with the prior art, the present application has at least the following beneficial effects:

The virus not only has broad-spectrum infectivity to various cells, and can be stably passaged, but also has green fluorescence, which can provide a research foundation for in vitro and in vivo virus tracing, virus detection, antiviral drugs screening, and vaccine preparation, with significant application prospects.

BRIEF DESCRIPTION OF DRAWINGS

Figure 1:
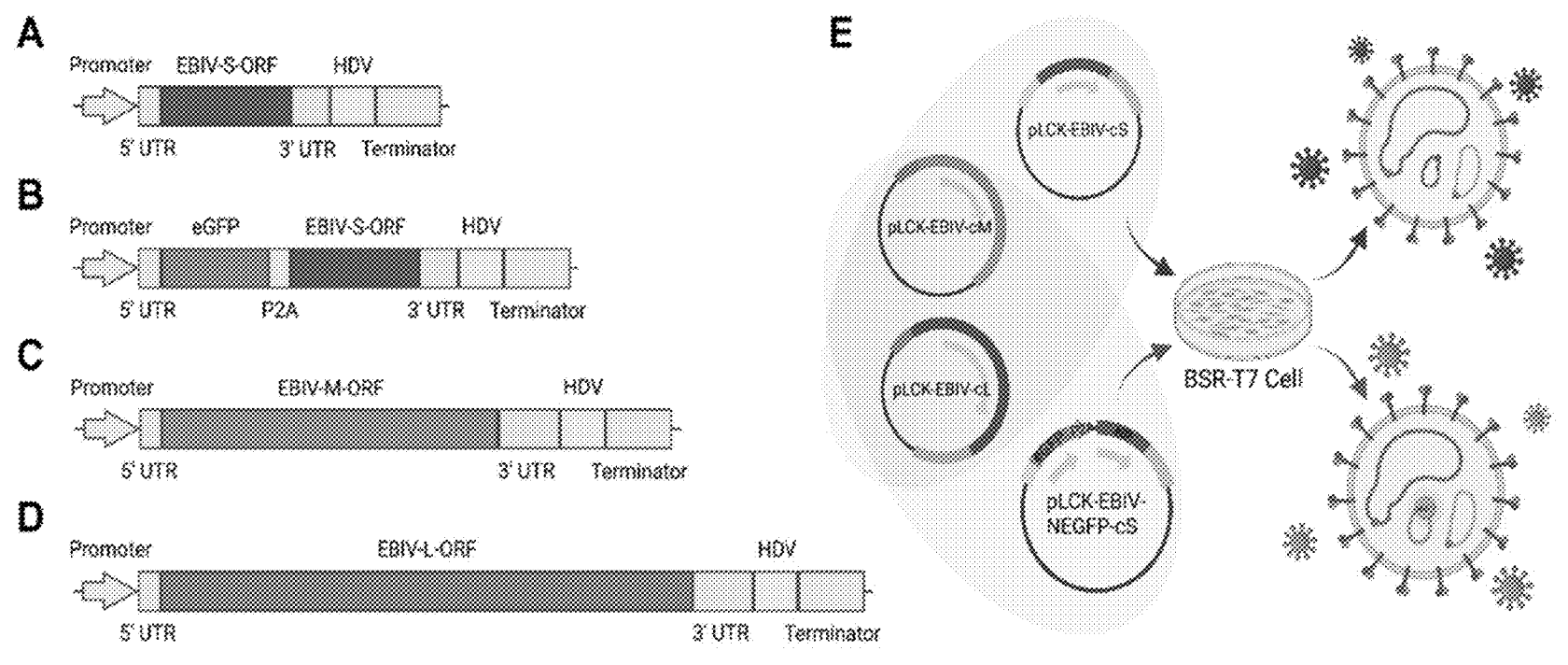

FIG. 1 shows schematic diagrams of the structures of recombinant plasmids used for constructing a recombinant EBIV provided in an embodiment of the present application; A: pLCK-EBIV-S plasmid; B: pLCK-EBIV-eGFP/S plasmid; C: pLCK-EBIV-M plasmid; D: pLCK-EBIV-L plasmid; E: Transfection strategy of recombinant EBIV.

FIG. 2 shows schematic diagrams of agarose gel electrophoresis of the PCR products of the L, M, and S segments of the recombinant EBIV, and the linearized pLCK plasmid provided in an embodiment of the present application.

DETAILED DESCRIPTION OF THE EMBODIMENTS

Figure 3:
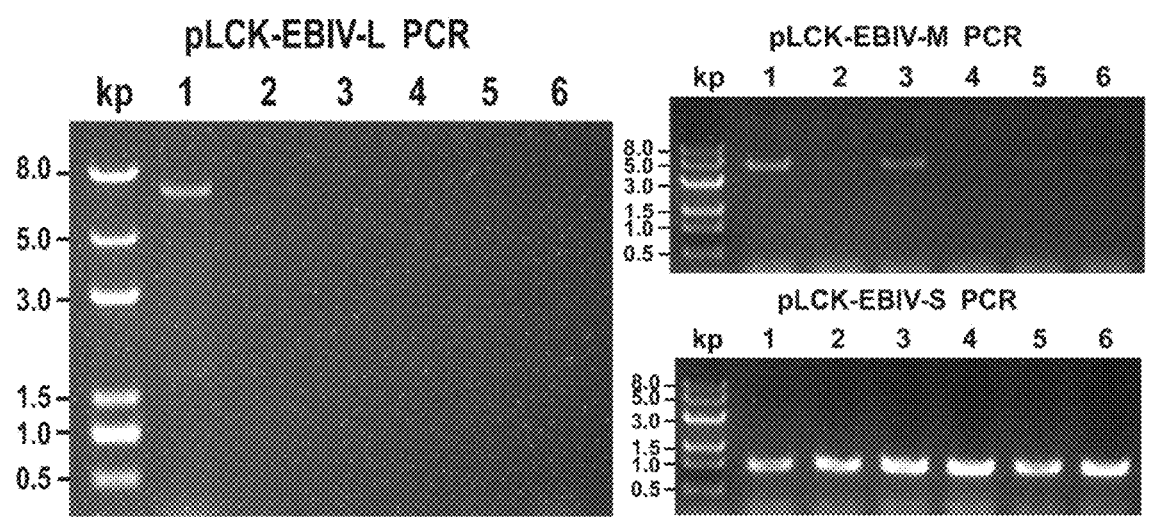
FIG. 3 shows schematic diagrams of agarose gel electrophoresis of the colony PCR products of the recombinant plasmid pLCK-EBIV-L, pLCK-EBIV-M, and pLCK-EBIV-S provided in an embodiment of the present application.

In order that the objects, aspects, and advantages of the present invention will become more apparent, a more particular description of the present invention will be rendered by reference to the embodiments. It should be understood that the particular embodiments described herein are illustrative only and are not restrictive. The reagents not described in detail separately in the present application are all conventional and can be obtained from commercial sources; Methods not specifically described in detail are conventional experimental methods and are known from the prior art.

Acquisition of EBIV Genome Sequence

The original EBIV strain used in the present application was isolated from *Culex modestus* by the Center for Disease Control and Prevention of Xinjiang Military Command. It was used to clone the L, M, and S segments of EBIV. The specific implementation process was as follows:

1. Materials

Source of strain: the original strain was isolated from *Cx. modestus* by the Center for Disease Control and Prevention of Xinjiang Military Command. The Cx. Modestuses were washed with PBS 3 times, added with 2 mL of DMEM medium, and repeatedly ground. The ground product was centrifuged for 5 min at 3000 r/min. The supernatant was filtered by a 0.22 μm filter membrane. The filtered supernatant (1 mL) was added into BHK-21 cells (the cells were cultured in a 25 cm² cell culture flask). After adsorption at 37° C. for 1 h, the supernatant was removed and 5 mL of DMEM medium containing 2% fetal bovine serum (v/v) was added into the cell culture flask. The flask was placed in a 5% $CO_2$ incubator for culture for more than 3 d. Olympus IX51 microscope was used to observe the cytopathic effect every day. The virus supernatant was absorbed and stored at −80° C. Source of cells: BHK-21 cells, Item No: C1-0034; specification: 1×10⁶ cells/T25 culture flask, Procell Life Science & Technology Co., Ltd., Wuhan.

2. RT-PCR

The EBIV isolate was serially diluted and inoculated into BHK-21 medium (cell concentration: 1×10⁶ cells/mL) at an inoculum with a multiplicity of infection (MOI) of 0.01. After 72 h of culture at 37° C., the viruses were harvested. The QIAamp® Viral RNA Mini KIT (Qiagen) was used to extract virus RNA. The GoScript™ Reverse Transcription System (Promega) was used to synthesize cDNA, which is used as a template for PCR amplification using KOD One™ PCR Master Mix Blue (TOYOBO). The PCR reaction system of 50 μL: 2× Reaction Mix Buffer, 25 μL, 10 μM Forward Primer, 2 μL, 10 μM Reverse Primer, 2 μL, Template DNA, 1 μL, and Nuclease-Free Water, 20 μL. The amplification condition: 98° C. for 10 s, 57° C. for 5 s, and 68° C. for 5 s, for 25 cycles. Among them, all the primer were generated and provided by Tsingke Biotechnology Co., Ltd., Beijing.

Figure 2:
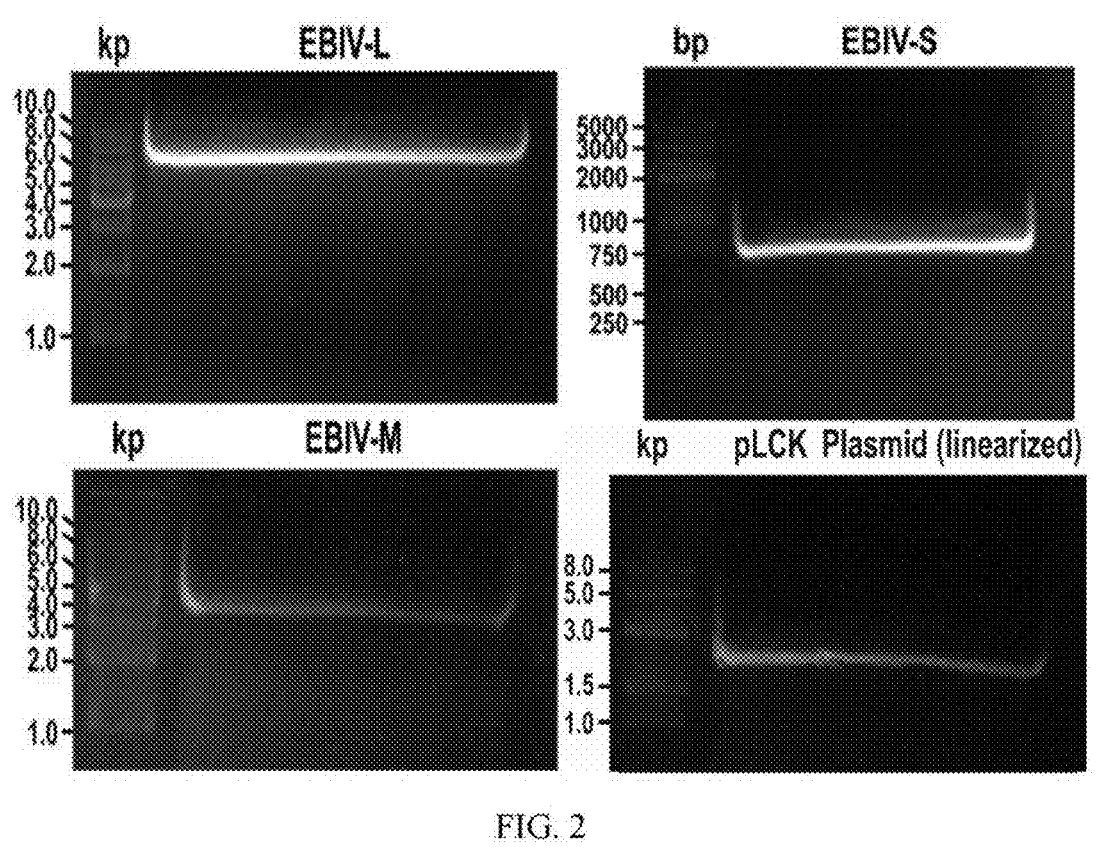

The results are shown in FIG. 2. The amplified products were detected by agarose gel electrophoresis and sequenced. The PCR product amplified with L-F and L-R primers (shown in SEQ ID NO. 1 and 2) has a band at 6970 bp; the PCR product amplified with M-F and M-R primers (shown in SEQ ID NO. 3 and 4) has a band at 4591 bp; the PCR product amplified with S-F and S-R primers (shown in SEQ ID NO. 5 and 6) has a band at 1002 bp. These are L, M, and S segments of EBIV, successively, and the nucleotide sequences are shown in SEQ ID NO. 14-16.

Construction of Recombinant Plasmids

1. Construction of pLCK-EBIV-L, pLCK-EBIV-M and pLCK-EBIV-S

Through the method of homologous recombination, L, M, and S sequence fragments were respectively ligated with linearized pLCK plasmids using ClonExpress® II One Step Cloning Kit (Vazyme) to obtain plasmids pLCK-EBIV-L, pLCK-EBIV-M and pLCK-EBIV-S. The ligation reaction system of 20 μL: 5×CE II Buffer 4 μL, Exnase II 2 μL, pLCK 46 ng, L fragment 280 ng, and dd$H_2O$ to 20 μL. The reaction condition: 37° C. for 30 min.

Transformation procedures of three plasmids: 5 μL of each of the three ligation reactants (pLCK-EBIV-L, pLCK-EBIV-M and pLCK-EBIV-S) into one of three tubes containing XL10 (Vazyme) was added into competent cells respectively. The tubes containing cells were kept into the ice for 30 min and were heat shock at 42° C. for 90 s. Then they were put into ice for 2 min again. After that, each tube containing cells were then added with 900 mL of LB medium and incubated in a shaker of 200 rpm at 37° C. for 1 h. Subsequently, the bacterial cells was coated on a plate containing kanamycin and cultured in an incubator at 37° C. overnight.

Colony PCR procedures of three plasmids: after the colonies on the plate grew to a visible size, one colony was picked, put into a tube containing 300 μL of LB medium, and the tubes were shaken at 220 rpm for 3-4 h at 37° C. Then, 2 μL bacterial solution was aspirated for colony PCR.

Colony PCR: colony PCR amplification reactions were performed using 2× Rapid Taq Master Mix (Vazyme), the reaction system of 50 μL: 2× Rapid Taq Master Mix 25 μL, each of upstream and downstream primers (see L-F/R, M-F/R, and S-F/R in the primer table 1) 2 μL, bacterial solution 2 μL, ddH$_2$O 19 μL. The amplification condition: 95° C. for 3 min, 95° C. for 15 s, 60° C. for 15 s, 72° C. for 1 min, for 35 cycles, and 72° C. for 5 min.

As shown in FIG. 2, the PCR product amplified by pLCK-F and pLCK-R primers (shown in SEQ ID NO. 7 and 8) has a band at 2319 bp, which is the amplification product of the pLCK null vector. As shown in FIG. 3, colony PCR results for plasmids pLCK-EBIV-L, pLCK-EBIV-M, and pLCK-EBIV-S show bands at 6970 bp, 4591 bp and 1002 bp, respectively, demonstrating successful plasmid ligation.

2. Construction of pLCK-EBIV-eGFP/S

In this step, since the length of the self-cleaved polypeptide 2A sequence (P2A sequence) of Porcine teschovirus 1 is too short, only 66 bp, which is not convenient for gel recovery, the sequences were added into primers eGFP-R and CS-F, respectively, and then inserted into the plasmid by homologous recombination. The sequences of the primers used are shown in Table 1.

TABLE 1

| Primer Name | Sequence |
|---|---|
| eGFP-F | cttttcaatggtgagcaagggcgaggag, as shown in SEQ ID NO. 9 |
| eGFP-R | ctccagcctgcttcagcaggctgaggttagtagctccgc ttccttgtacagctcgtccatgccgag, as shown in SEQ ID NO. 10; The underline represents the first 43 nucleotides of the P2A sequence in the 5' to 3' direction; The bold represents the part overlapping with the CS-F primer; |
| CS-F | cctgctgaagcaggctggagacgtggaggagaaccctggac ctttggagctagaatttgaagatgtccctactaac, as shown in SEQ ID NO. 11; The underline represents the last 43 nucleotides of the P2A sequence in the 5' to 3' direction; The bold represents the portion overlapping the eGFP-R primer. |
| CS-R | cgcccttgctcaccattgaaaaagaaagaataagtcaaagact caaatcctctagtag, as shown in SEQ ID NO. 12 |
| P2A | ggaagcggagctactaacttcagcctgctgaagcaggctggag acgtggaggagaaccctggacct, as shown in SEQ ID NO. 13 |

(1) Obtain eGFP Fragment

Figure 4:
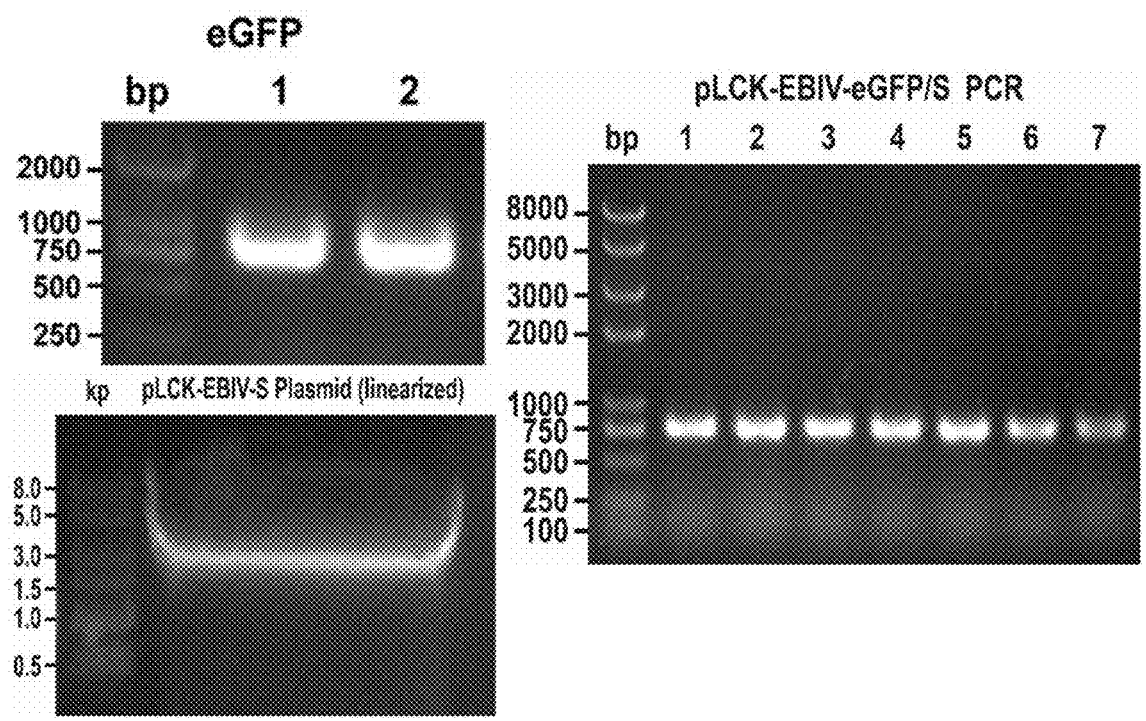
FIG. 4 shows schematic diagrams of agarose gel electrophoresis of the PCR products of the eGFP fragment and the linearized recombinant plasmid pLCK-EBIV-S, and the colony PCR product of the recombinant plasmid pLCK-EBIV-eGFP/S provided in an embodiment of the present application.

The plasmid pcDNA3.1-eGFP (Biofeng) carrying eGFP was used as a template for amplification using KOD One™ PCR Master Mix-Blue (TOYOBO) and the primers (eGFP-F and eGFP-R) shown in the primer table 1 to obtain a specific fragment of eGFP (as shown in SEQ ID NO. 17). As shown in FIG. 4, the band size is 768 bp. The amplified DNA fragment was recovered in a conventional manner to obtain the eGFP fragment.

The PCR reaction system of 50 μL: 2× Reaction Mix Buffer, 25 μL, 10 μM eGFP-F, 2 μL, 10 μM eGFP-R, 2 μL, Template DNA, 1 μL, and Nuclease-Free Water, 20 μL. The amplification condition: 98° C. for 10 s, 57° C. for 5 s, 68° C. for 30 s, for 25 cycles.

(2) Obtain Linearized pLCK-EBIV-S Fragment

The pLCK-EBIV-S plasmid was used as a template for amplification using KOD One™ PCR Master Mix-Blue (TOYOBO) and the primers (CS-F and CS-R) as shown in Table 1. The result is shown in FIG. 10, and the band size is 3327 bp. The amplified DNA fragment was detected and recovered in a conventional manner to obtain the pLCK-EBIV-S (linearized) fragment.

The PCR reaction system of 50 μL: 2× Reaction Mix Buffer, 25 μL, 10 μM CS-F, 2 μL, 10 μM CS-R, 2 μL, Template DNA, 1 μL, and Nuclease-Free Water, 20 μL. The amplification condition included: 98° C. for 10 s, 57° C. for 5 s, 68° C. for 30 s, for 25 cycles.

(3) Construction of pLCK-EBIV-eGFP/S Plasmid

Since P2A was only 66 bp, it was added to primers eGFP-R and CS-F and both were inserted into the vector by homologous recombination. The reaction system for homologous recombination of 20 μL: 5× Reaction Buffer, 4 μL, eGFP fragment, 30 ng, cS fragment, 60 ng, Enzyme, 2 μL, and Nuclease-Free Water, 33 μL. The reaction condition: 37° C. for 30 min. Transformation of the ligation product was performed by using XL10 competent cells. The cultured single colony was subjected to colony PCR using primers eGFP-F and eGFP-R. The results are shown in FIG. 4, and the band size is about 760 bp. The positive clone identified by colony PCR of the eGFP was cultured and the plasmid was extracted for sequencing. The correct clone was named pLCK-EBIV-eGFP/S.

Preparation of Recombinant EBIV

In this example, the sequences of pLCK-EBIV-L, pLCK-EBIV-M, and pLCK-EBIV-eGFP/S after sequencing are as shown in SEQ ID NO. 18-20. The three plasmids were co-transfected into BSR-T7 cells (RE59683, Sciencell) to generate the recombinant EBIV.

1. Preparation Method

The concentrations of plasmids pLCK-EBIV-eGFP/S, pLCK-EBIV-M, and pLCK-EBIV-L were determined by Nanodrop; BSR-T7 cells were prepared and inoculated into 12-well cell culture plate (the number of cells in each well was $2\times10^5$). The cells were cultured in a cell incubator with a temperature of 37° C. and a $CO_2$ concentration of 5% until the cell confluence was 40-50%. The plasmids pLCK-EBIV-eGFP/S, pLCK-EBIV-M, and pLCK-EBIV-L were mixed in a mass ratio of 1:1:1 and 1:2:3 (the total mass of mixed plasmids was 1.5 mg). Then the mixed plasmids were added into 100 μL of serum-free medium (Gibco Opti-MEM), and then added with 4.5 μL of transfection reagent (Item No. MIR 2305, specification 5×1 mL, Minis). The mixture was gently mixed well and then incubated at room temperature for 15-30 min. The medium of BSR-T7 cell was changed into the DMEM medium containing 2% FBS. Then, the above-mentioned transfection mixture was gently dropped into the wells. The control group cells were added with the same amount of null vector plasmid transfection mixture. The cell plate was placed into a cell incubator with a temperature of 37° C. and a $CO_2$ concentration of 5% for culture. After transfection, the cell status and fluorescence expressions of the experimental group and control group were observed by Olympus inverted fluorescence microscope every 24 h. Rescue efficiency (%)=the number of wells showing cytopathic effect/number of experimental wells×100%.

The detection of virus titer: the rescued virus was diluted to $10^{-6}$ with a 10-fold gradient with DMEM medium. Add 100 μL of virus dilution into a 24-well cell culture plate containing BHK-21 cell monolayer at 37° C. After incubation for 1 h, remove virus dilution and add 500 μL DMEM cover containing 1.0% sodium carboxymethyl cellulose. The culture was performed in a 37° C. incubator for 3 d. After that, cells were immobilized with 3.7% formaldehyde overnight, and stained with 2% crystal violet to count the number of plaques. Virus titer (PFU/mL)=the number of plaques/(dilution factor×inoculation volume per well).

2. Results

Figure 5:
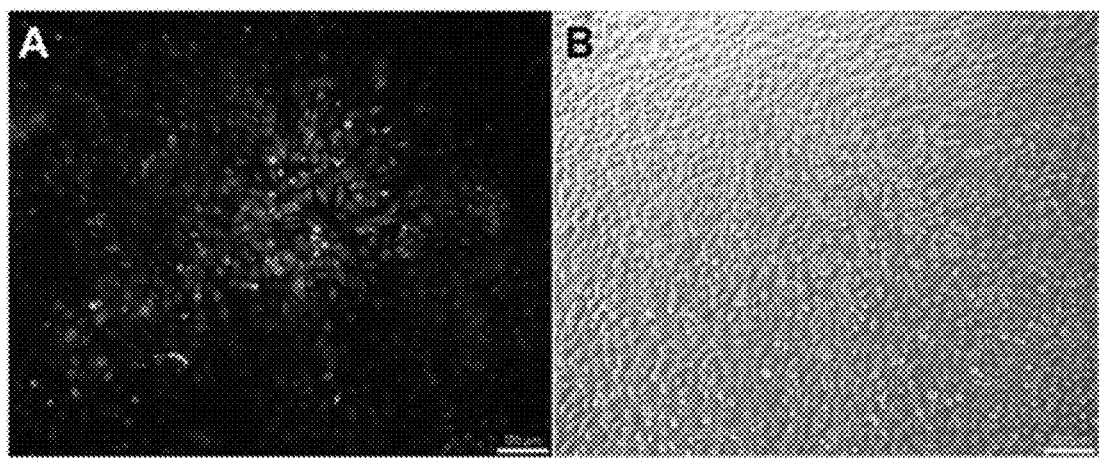
FIG. 5 shows schematic diagrams of cells infected by a recombinant EBIV as provided in an embodiment of the present application; A: image of virus-infected cell under UV excitation; B: image of virus-infected cell under bright field.
Figure 6:
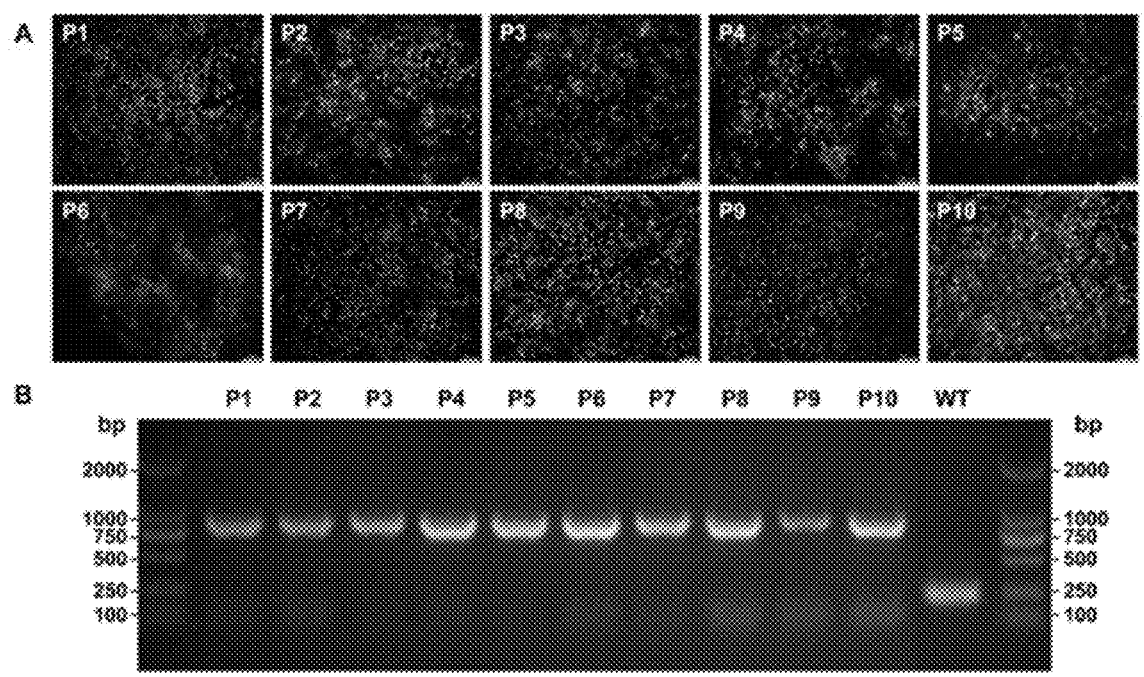
FIG. 6 shows the fluorescence stability of recombinant EBIV after 10 serial passages in BHK-21 cells as provided in an embodiment of the present application; A: image of P1-P10 virus-infected BHK-21 cells (under UV light excitation); B: schematic representation of agarose gel electrophoresis of the RT-PCR products for the P1-P10 viruses after RNA extraction.

As a result, as shown in FIG. 5, green fluorescence was clearly observed in the experimental group after excitation with 405 nm excitation light, while no fluorescence was observed in the control group, thus indicating that the recombinant virus can express the green fluorescent protein according to the above procedures.

TABLE 2

| Three-plasmid rescue ratio | Number of wells showing the cytopathic effect | Total number of experiment wells | Rescue efficiency | Average virus titer (PFU/mL) |
| --- | --- | --- | --- | --- |
| 1:1:1 | 3 | 10 | 30% | $4.20 \times 10^5$ |
| 1:2:3 | 7 | 10 | 70% | $4.15 \times 10^5$ |

At the same time, according to the results in Table 2, when the co-transfection ratio of pLCK-EBIV-eGFP/S, pLCK-EBIV-M and pLCK-EBIV-L plasmids is 1:2:3, the rescue efficiency of recombinant EBIV is higher than that of the co-transfection ratio of 1:1:1. Furthermore, in the present application, the constructed recombinant EBIV (named as green fluorescent-labeled recombinant EBIV, rEBIV/eGFP/S) was deposited at the China Center for Type Culture Collection on Jan. 25, 2022, with the deposit address of Wuhan University, Wuhan, China (address of No. 299, Bayi Road, Wuhan City, Hubei Province), and Deposit Number of CCTCC NO. V202204.

Continuous Passage of Recombinant EBIV

Furthermore, the present application also studies the stability of the fluorescence signal of the continuous passaged recombinant EBIV. The specific steps were as follows.

1. Materials and Methods (1) A 6-well plate for BHK-21 cells (hamster kidney cells, Procell Life Science&Technology Co., Ltd, Wuhan) was prepared. DMEM medium (Gibco) containing 10% FBS (Gibco) was used as a culture medium. The experiment would be conducted when the cells grew to 40-50%.

(2) 100 μl of the recombinant EBIV obtained above was added into BHK-21 cells, which were then incubated in a 37° C. incubator for 1 h. Remove the cell supernatant and add DMEM medium containing 2% FBS. The cell plate was placed in an incubator with a temperature of 37° C. and a $CO_2$ concentration of 5% for culture. Cell fluorescence and cell status were observed every 24 hours. After the cells developed the cytopathic effect, the cell supernatant was inoculated into new cells. The virus was serially passaged for 10 generations to observe whether its fluorescence was stable.

(3) the RNA of each generation of the P1-P10 virus was extracted to RT-PCR.

(4) RNA Extraction: 200 μL of each generation of P1-P10 virus was collected. S-48 flux nucleic acid extractor (NanoMagBio) and its matching kit, magnetic bead method virus RNA extraction kit (NanoMagBio) were used to perform RNA extraction.

(5) RT-PCR: RT-PCR amplification reactions were performed using PrimeScript™ One Step RT-PCR Kit Ver. 2 (Dye Plus) (Takara). The system of 50 μL: 2× One Step Buffer (Dye Plus), 25 μL, PrimeScript one Step Enzyme Mix, 2 μL, each of upstream and downstream primers (see eGFP-Test-F/R in Primer Table 1), 1 μL, each of RNA of P1-P10, 1 μL, and RNase Free $dH_2O$, 20 μL. The amplification condition: 50° C. for 30 min, 94° C. for 2 min, 94° C. for 30 s, 55° C. for 30 s, for 35 cycles, and 72° C. for 1 min.

2. Results

The results shown in FIG. 6 indicate that the eGFP gene is stably present in P1-P10 and can express the green fluorescent protein.

Application of Antiviral Drug Screening

Further, the recombinant EBIV disclosed in the examples of the present application can also be used for the screening of antiviral drugs, for example for the screening of antiviral compounds. The specific steps were as follows.

(1) A 96-well plate for BHK-21 cells was prepared. The cells were planked at $10^4$ cells/well. The plate was cultured in a cell incubator with a temperature of 37° C. and a $CO_2$ concentration of 5%. The drug screening test was conducted when the cells grew to 40-50%. The drug to be tested was dissolved in dimethyl sulfoxide. Then the drug was diluted to 100 μM with DMEM medium containing 2% FBS. After that, the drug was subjected to serial 2-fold dilution to obtain the dilution gradient with the concentration of 100 μM, 50 μM, 25 μM, 12.5 μM, 6.25 μM, 3.125 μM, and 1.5625 μM, respectively (the concentration of DMSO in the diluted drug shall be <0.1%).

(2) The original culture medium was removed from the 96-well plate. The virus was inoculated into the 96-well plate at an MOI of 0.01 and a volume of 100 μL/well. At the same time, the diluted drugs to be tested were respectively added into the same 96-well plate at 100 μL/well and mixed well with the virus solution. The plate was incubated in a cell incubator with a temperature of 37° C. and a $CO_2$ concentration of 5% for 36 hours before detection.

(3) The 96-well plate was photographed and data was analyzed using a high content screening (HCS) system to determine the amount of fluorescence per well and calculate the Z-factor for each compound:

$$Z = 1 - \frac{3(\sigma_s + \sigma_c)}{|\mu_s - \mu_c|},$$

where the four parameters $\sigma_s$, $\sigma_c$, $\mu_s$, and $\mu_c$ represent the standard deviation and mean of the sample to be tested (s) and the negative (c) control, respectively. The stability and sensitivity of the screening system were then assessed using the Z'-factor:

$$Z' = 1 - \frac{3(\sigma_p + \sigma_n)}{|\mu_p - \mu_n|},$$

where the four parameters $\sigma_p$, $\sigma_n$, $\mu_p$, and $\mu_n$ represent the standard deviation and mean of the positive sample (p) and the negative (n) control, respectively.

(4) Cell viability per well (and the percentage of cells remaining per well) was observed under a microscope and the half-maximal effect concentration (EC50) of the drug was calculated using GraphPad Prism 9 software and an EC50 graph was plotted.

Figure 7:
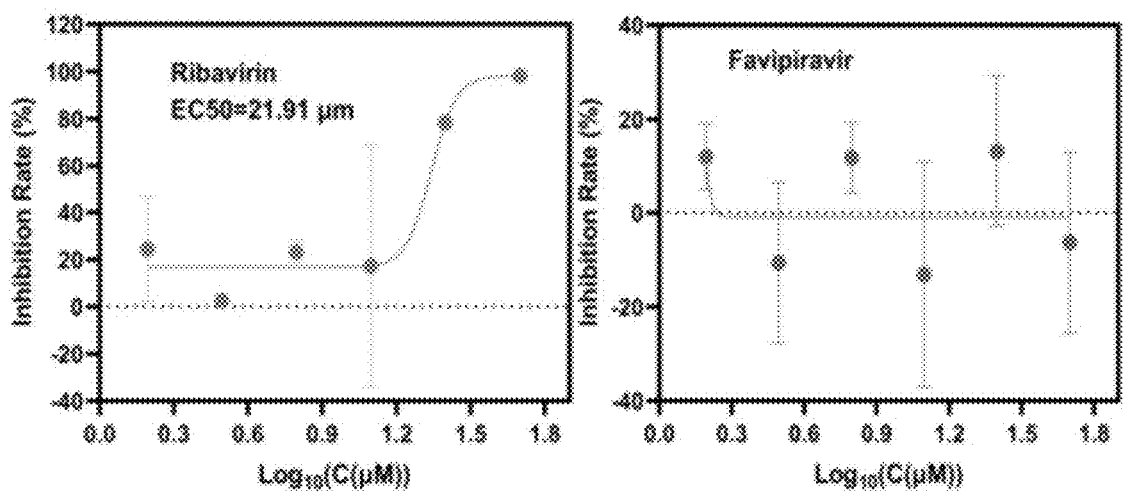
FIG. 7 shows the EC50 (half-maximal effect concentration) values of ribavirin and favipiravir against recombinant EBIV carrying green fluorescent protein; the abscissa is the common logarithm of the drug concentration and the ordinate is the inhibition rate.

As can be seen in FIG. 7, the EC50 of ribavirin is 21.91 μM, while favipiravir has no inhibitory effect on the virus even at 50 μM, so 25 μM of ribavirin is selected as a positive control to perform high-content screening for other drugs to be screened. The Z'-factor for this system was calculated to be 0.46, which is within an acceptable range for compounds where the Z-factor is greater than the Z'-factor, as shown in Table 3. In Table 3, the Z-factors of clinodiside A, diosmin, and secoxyloganin are the largest and the cell activities are all 100%, indicating that clinodiside A, diosmin, and secoxyloganin are potential anti-recombinant EBIV drugs.

TABLE 3

| Drug Name | Z-factor | Cell viability |
| --- | --- | --- |
| Psoralidin | 0.46 | 50% |
| Isobavachalcone | 0.58 | 30% |
| Epigallocatechol | 0.51 | 0% |
| Cantharidin | 0.50 | 50% |
| Chenodeoxycholic acid | 0.59 | 70% |
| Beta, beta-dimethyl acryl shikonin | 0.53 | 70% |
| Clinodiside Aogenin A | 0.54 | 100% |
| Diosmin | 0.58 | 100% |
| Secoxyloganin | 0.56 | 100% |

The above experimental results prove that the recombinant EBIV stably carrying the green fluorescent protein in the present application can provide a research basis for in vivo and in vitro virus tracing, virus detection, antiviral drugs, and vaccine screening, and has a very important application prospect.

The above is only the preferred specific implementation method of this application, and the scope of this application is not limited to this. Any changes or replacements that can be easily thought of by technical personnel familiar with the technical field within the scope of the disclosure in this application should be covered within the scope of this application.

What is claimed is:

1. A method for preparing a recombinant Ebinur Lake virus (EBIV) strain labeled with GFP fluorescence, comprising the following steps:

Cloning genes shown in SEQ ID NO. 14-16, wherein primers used for amplifying the gene sequences were shown in SEQ ID NO. 14 are as shown in SEQ ID NO. 1 and 2; primers used for amplifying the genes shown in SEQ ID NO. 15 are shown in SEQ ID NO. 3 and 4; primers used for amplifying the genes shown in SEQ ID NO. 16 are shown in SEQ ID NO. 5 and 6;

Ligating the genes shown in SEQ ID NO. 14-16 respectively to a linearized pLCK plasmid to obtain pLCK-EBIV-L, pLCK-EBIV-M, and pLCK-EBIV-S plasmids;

Using pcDNA3.1-eGFP as a template, and eGFP-F and eGFP-R as primers to clone an eGFP fragment;

Using pLCK-EBIV-S as a template, and CS-F and CS-R as primers to clone a linearized fragment of pLCK-EBIV-S;

Ligating the eGFP fragment and the linearized fragment of pLCK-EBIV-S by homologous recombination to obtain a recombinant plasmid pLCK-EBIV-eGFP/S; wherein the eGFP fragment is ligated to pLCK-EBIV-S using P2A; the nucleic acid sequence of the P2A is shown in SEQ ID NO. 13; the nucleotide sequence of the eGFP fragment is shown in SEQ ID NO. 17;

Mixing pLCK-EBIV-eGFP/S, pLCK-EBIV-M, and pLCK-EBIV-L in a mass ratio of 1:2:3, and co-transfect them into BSR-T7 cells and culture same, and harvest the transfected culture, wherein the culture contains the recombinant EBIV strain labeled with GFP fluorescence;

wherein a method for constructing pLCK-EBIV-eGFP/S comprises:

Cloning eGFP using primers eGFP-F and eGFP-R shown in SEQ ID NO. 9 and 10 from plasmid pcDNA3.1-eGFP to obtain the eGFP fragment shown in SEQ ID NO. 17; wherein the PCR reaction system of 50 μL: 2× Reaction Mix Buffer, 25 μL, 10 μM eGFP-F, 2 μL, 10 μM eGFP-R, 2 μL, Template DNA, 1 μL, and Nuclease-Free Water, 20 μL; the PCR amplification reaction: 98° C. for 10 s, 57° C. for 5 s, 68° C. for 30 s, 16° C. for 10 min; the number of cycles of 25;

Cloning the pLCK-EBIV-S plasmid by using primers CS-F and CS-R shown in SEQ ID NO. 11 and 12 to obtain a linearized pLCK-EBIV-S fragment; wherein the PCR reaction system of 50 μL: 2× Reaction Mix Buffer, 25 μL, 10 μM CS-F, 2 μL, 10 μM CS-R, 2 μL, Template DNA, 1 μL, and Nuclease-Free Water, 20 μL; the PCR reaction condition: 98° C. for 10 s, 57° C. for 5 s, 68° C. for 30 s, 16° C. for 10 min; the number of cycles of 25;

Ligating the eGFP fragment and the pLCK-EBIV-S linearized fragment by homologous recombination to obtain pLCK-EBIV-eGFP/S, wherein the reaction system for the homologous recombination of 20 μL: 5× Reaction Buffer, 4 μL, eGFP fragment, 30 ng, cS fragment, 60 ng, Enzyme, 2 μL, and Nuclease-Free Water, 33 μL; the homologous recombination reaction conditions: 37° C. for 30 min, and 16° C. for 10 min.

2. A plasmid composition for constructing a recombinant EBIV, comprising three recombinant plasmids, pLCK-EBIV-L, pLCK-EBIV-M, and pLCK-EBIV-eGFP/S, wherein the nucleotide sequences of the three recombinant plasmids are successively shown in SEQ ID NO. 18, 19 and 20; wherein the target gene included in the pLCK-EBIV-L recombinant plasmid is EBIV L fragment, the nucleotide sequence of which is shown in SEQ ID NO. 14; the target gene included in the pLCK-EBIV-M recombinant plasmid is the EBIV M fragment, the nucleotide sequence of which is shown in SEQ ID NO. 15; the target gene included in the recombinant plasmid of pLCK-EBIV-eGFP/S is the EBIV S fragment and green fluorescent protein gene fragment, the nucleotide sequences of which are shown in SEQ ID NO. 16 and 17, respectively; three recombinant plasmids are obtained by ligating the target genes and the linearized pLCK plasmid; and in the plasmid composition, pLCK-EBIV-eGFP/S, pLCK-EBIV-M, and pLCK-EBIV-L are transfected into cells at a mass ratio of 1:2:3 to rescue a recombinant EBIV strain.

3. A recombinant EBIV strain prepared by the method of claim 1; the recombinant EBIV strain was deposited at the China Center for Type Culture Collection on Jan. 25, 2022, with the deposit address of Wuhan University, Wuhan, China (address of No. 299, Bayi Road, Wuhan City, Hubei Province), and the deposit number of CCTCC NO. V202204.

4. A recombinant host bacterium comprising the recombinant plasmid of the plasmid composition of claim 2.

5. Use of the plasmid composition of claim 2, comprising at least one of the preparation of a recombinant EBIV, expression of a protein associated with the recombinant EBIV, screening for drugs that antagonize EBIV, in vitro tracing of a recombinant EBIV, preparation of a vaccine against EBIV, and preparation of a product associated with detection of EBIV.

* * * * *

SEQUENCE LISTING

```
Sequence total quantity: 20
SEQ ID NO: 1            moltype = DNA  length = 50
FEATURE                 Location/Qualifiers
source                  1..50
                        mol_type = other DNA
                        organism = synthetic construct
SEQUENCE: 1
acgactcact atagagtagt gtactcctat atataaaaat taaaaatatc                50

SEQ ID NO: 2            moltype = DNA  length = 40
FEATURE                 Location/Qualifiers
source                  1..40
                        mol_type = other DNA
                        organism = synthetic construct
SEQUENCE: 2
ccatgccgac ccagtagtgt gctcctatat ataaaaattg                           40

SEQ ID NO: 3            moltype = DNA  length = 47
FEATURE                 Location/Qualifiers
source                  1..47
                        mol_type = other DNA
                        organism = synthetic construct
SEQUENCE: 3
atacgactca ctatagagta gtgtactacc gatatacaca aaccaat                   47

SEQ ID NO: 4            moltype = DNA  length = 39
FEATURE                 Location/Qualifiers
source                  1..39
                        mol_type = other DNA
                        organism = synthetic construct
SEQUENCE: 4
atgccgaccc agtagtgtgc taccgataaa agcaaacac                            39

SEQ ID NO: 5            moltype = DNA  length = 46
FEATURE                 Location/Qualifiers
source                  1..46
                        mol_type = other DNA
                        organism = synthetic construct
SEQUENCE: 5
acgactcact atagagtagt gtactccacg cataaaactt tttatc                    46

SEQ ID NO: 6            moltype = DNA  length = 40
FEATURE                 Location/Qualifiers
source                  1..40
                        mol_type = other DNA
                        organism = synthetic construct
```

```
SEQUENCE: 6
atgccgaccc agtagtgtgc tccaccttaa acttaaacdd                              40

SEQ ID NO: 7              moltype = DNA   length = 32
FEATURE                   Location/Qualifiers
source                    1..32
                          mol_type = other DNA
                          organism = synthetic construct
SEQUENCE: 7
gcacactact gggtcggcat ggcatctcca cc                                      32

SEQ ID NO: 8              moltype = DNA   length = 44
FEATURE                   Location/Qualifiers
source                    1..44
                          mol_type = other DNA
                          organism = synthetic construct
SEQUENCE: 8
aggagtacac tactctatag tgagtcgtat taatttcgcg ggat                         44

SEQ ID NO: 9              moltype = DNA   length = 29
FEATURE                   Location/Qualifiers
source                    1..29
                          mol_type = other DNA
                          organism = synthetic construct
SEQUENCE: 9
cttttcaat ggtgagcaag ggcgaggag                                           29

SEQ ID NO: 10             moltype = DNA   length = 67
FEATURE                   Location/Qualifiers
source                    1..67
                          mol_type = other DNA
                          organism = synthetic construct
SEQUENCE: 10
ctccagcctg cttcagcagg ctgaagttag tagctccgct tcccttgtac agctcgtcca        60
tgccgag                                                                  67

SEQ ID NO: 11             moltype = DNA   length = 76
FEATURE                   Location/Qualifiers
source                    1..76
                          mol_type = other DNA
                          organism = synthetic construct
SEQUENCE: 11
cctgctgaag caggctggag acgtggagga gaaccctgga cctttggagc tagaatttga        60
agatgtccct actaac                                                        76

SEQ ID NO: 12             moltype = DNA   length = 58
FEATURE                   Location/Qualifiers
source                    1..58
                          mol_type = other DNA
                          organism = synthetic construct
SEQUENCE: 12
cgcccttgct caccattgaa aagaaagaa taagtcaaag actcaaatcc tctagtag           58

SEQ ID NO: 13             moltype = DNA   length = 66
FEATURE                   Location/Qualifiers
source                    1..66
                          mol_type = other DNA
                          organism = synthetic construct
SEQUENCE: 13
ggaagcggag ctactaactt cagcctgctg aagcaggctg agacgtgga ggagaaccct         60
ggacct                                                                   66

SEQ ID NO: 14             moltype = DNA   length = 6970
FEATURE                   Location/Qualifiers
source                    1..6970
                          mol_type = other DNA
                          organism = synthetic construct
SEQUENCE: 14
acgactcact atagagtagt gtactcctat atataaaaat taaaaatatc aaattgttct        60
gaacatggag gatccaatgt atgagcagtt cttacaaagg atccaagcag tcagaacagc       120
tactgtggct aaggacatca gtgctgacat actggaggca agacatgatt actttgggcg       180
agagctctgc cgagcattgg acattgagta tagaaacaat gttttgcttg atgagataat       240
attggacgtt tatccaggag ttaaccttat ggagtataat gttccacatg ttaccctga       300
taattatatc tggactgggg atatgttgct gatattagac tacaaagtct ctgttgggca      360
tgatagtact gaagtgacat acaaaaata tacaacacta atcctccag tcatgcaaga       420
aattggtata aacacagaaa tttgcattat aagggcaaat ccagttacaa atcaaataag       480
cattgttggt gagcaattta acgattgtt ccaacaatt cctgtcgagc tcaatttgc         540
aagatttttt gaactaagaa aaatgctctt agataaattt gctgatgatg aagaattttt       600
aatgatgata gctcatggtg actttacctt gactgcaccct ggtgccagg atgatactcc      660
```

```
tgaactaata gaccatccta tataccaaga gtttcttggc tctatgcccc cacgatttgt   720
atcaatgttt gaagaagcca tggacttag tgcatacaat gcggagcgct ggaatacact   780
actatataaa ataaaaaact tgactcttga ggattaccaa gattatttga atataaagtc   840
ccacaacata tttaatatga caggagattt tatgaagccg actcaagatg aaatagatat   900
tggctgggaa tccatgagta agagaatatc acaagagaga gagttgacca cagatataaa   960
taaacaaaaa ccttcaatac atttcatctg ggcgcaaaat aaagatagga agttgttaaa  1020
ttccacagca aaactggtgt tcctatcaaa caccttacag agtataacag aacaatcaac  1080
ctggacagat gctttaaagg ctataggtgt tagtatggat attggtaata atattggatt  1140
gtatgaaaat ttatgtgctg agagaaagct aattgcacga tcaaccggta aaaaggttaa  1200
taataagaga ttagaagctg tcaaaatcgg gaaagccctt gtattgtggg aacaacagtt  1260
cattcttgct aatgaattat tcaaaggaca agaaagacaa aagtttataa aaaactttt  1320
tggtataggt aagcacaaaa ccttcaaaga taaaacatca gaagatcttg atagagaaaa  1380
gccaaaaatt ttagattta ataacactag agtactaatg gctgcaagga ctatggtgaa  1440
caaaaataaa aaatttctta gtcaagataa tacactagag tttgatcacc caattatatc  1500
aacttacttt gatcaagtaa gggaggcatc catagatact gcccaagtac tgaagaagat  1560
ctccaagaca tgttttggc aagccataac agacatatct acattaatga ggaacatctt  1620
agcagtctct caatacaata gacacaatac attccgcgtg gcaatgtgtg cgaatgattc  1680
aatatatggt cttgtgttc cttcttcaga cattaaaaca agagagcta caattgtctt  1740
ctgcattgtc tgtatgcata attctagaga tgacattatg gatgcaggtg cactatttac  1800
cactttggaa accaaaacta aaacattgt gtctataagt aaggcaatta gattggataa  1860
ggaaagatgt cagagaattg tctcatctcc tggcctattt attctcagca cactattatt  1920
atacaataac aatactgaaa tatcactata tgatgtcata aattttacat tctacactag  1980
cttgtcaata acaaaaagca tgctatctct aacagaacca tctagatata tgataatgaa  2040
ttcacttgca atatcagtc atgttagaga ttatatagca gaaaaattt ctccgtacac  2100
aaaaactttg ttcagtgtt atatggttaa cttgatcaag agaggctgtg ccactgccaa  2160
tgagcaatct gagaagatcc aagtcagaaa tatatatcta tcagattatg atataacgca  2220
aaaagggata aatgacatta gaaatttaga ctcgatatgg ttccccggca agttaatttt  2280
gaaggaatac ataaatcaaa tctatctacc atttatttc aatgcaaagg gactacatga  2340
aaaacatcat gttatgattg acttagcaaa gactgtttta gaaatagaaa tgaatcaaag  2400
gttagaccaa ttaggaattt ggtctaagaa tgaaaaaaaa caacatgtca atctgccaat  2460
tttggttcat tcaattgcta agtcattgat attagacaca tccagacaca accatctgag  2520
gaatagagtt gagagcagaa ataattttag gaggagcatc tcaaccatca gcacttttac  2580
aagctcaaaa tcttgtataa aaataggcga attccaagat ctgaaaacaa aagaatttaa  2640
agcaactaaa aaaatgaatg agaagataaa tcagaaattt agattagcca atccattgtt  2700
cattgatgat aaggatgctg atgcagaaat aatgcattgt aattatgatc agctgaaaac  2760
aaaagtaccg aattataagg attatatctc agttaaggtc tttgatagat tatatgagct  2820
ttacaaaaca aaggagcttg atgacaaacc atttatagaa caagcaatga agatgatgaa  2880
agagcataaa gaattcaatt tcacattctt taataaggga caaaaaacat ctaaggacag  2940
ggaatatttt gttggggagt ttgaagcaaa aatgtgcatg tatgttgttg aacgaatttc  3000
caaagaaaga tgcaagctga atgaagatga aatgatcagt gagcctgggg ataccaaact  3060
gagaatatta gaaaaaaaag cagaagagga gatcagatat atagttgaaa aaactaaaga  3120
tagtatttg aaaggagacc ctgcacatgc attaaaatta gaattaatg cagatatgtc  3180
aaaatggagt gcacaagatg tttcttcaa gtatttctgg ttggtagcaa tggatcctat  3240
actgtaccca tcggaaaaga agaggatttt atatttcatg tgcaattata tgcagaaaaa  3300
tttgatcctt ccggacgact tattatccaa tataatggat cagaggagac catatgagaa  3360
tgatataata ctagaatcaa ccaatggatt ggcacagaac tttgtgcaaa ttaaaagaaa  3420
ctggcttcaa ggtaatttca atatatgtc aagctatgct catagctgtg ctatgttagt  3480
atacaaagat gttgccaaag aggctgtaaa actgcttgat ggcaattgtt tagtgaattc  3540
tatggtgcac tctgacgata accaaacatc attgtccatc attcaaaaca aattaaagga  3600
taatatgatc atagaatatg tggcaaaact atttgaagca gtttgcttgg catttggttg  3660
ccaagccaac atgaagaaaa cctatatcac ccacacagc aaagagttg tctcactgtt  3720
caatttgcat ggtgagcctt tatcaatata tggcaggttc ttactaccaa gtgttggaga  3780
ttgtgcatat ataggtccct atgaagattt agcaagtagg ctgtccgccg cacaacaaag  3840
cttaaaacat ggttgtcctc caagttatgt ctgggttgcc attagttgta gccattggat  3900
aacgcatttc acttacaata tgatgcatga tcaagtcaac tctcccatgc agtatctacc  3960
gtttgaagat agattccaag tcccaactga attgaatgat tatttatctg caccattata  4020
tcttattgca ttaataggaa tagaggctga caatttatgg ttcctgttaa acatatttgaa  4080
gaaactagta ccattagata aacagaagga acaatacaa acacaattca ctgctattca  4140
agatatata aacaaattga caccttctga gttatttaga ttaaagttgc taagatatct  4200
gacattggac acagagataa catcagactc caacatggga gagacaagtg atatgaggag  4260
taggtctta ttaacaccaa ggaaattcac aactgcaggc tcactaaata aattggtatc  4320
ctacaatgat ttcaagaatg ctatgaatac aaatgaattt caagagaact tagaatatat  4380
ggaaatgaat ccagaacttc ttgtcacaaa aggcgaaaat aaagaacaat atataaactc  4440
catcttattt agatataact caaagagatt taaagaaagc ttatcaatac aagcaccttc  4500
acaactcttt gttgagcaga tactatttc ccataagcct attattgatt atagtagtat  4560
ctttgacaaa ctagcatcta tggcagagac agaaataata gagaacttac cagacattat  4620
tggtagagtc acctacctc aggcatatca atgataacg agagatataa cacaattacc  4680
tctgatatt gatgacataa agatcgtatt caagtattgt gtattaaatg acccattaat  4740
tatcactgct gctaatacat ccttgctctg tgtgagaggt gcgccacaag atagaactgg  4800
attaagtgca tgccaaatgc cagaattccg taatatgaaa ctcatacatc attccaccagc  4860
actagttctc aaggcatta gtaaggggac agtagatata cctggtgcag accctgtaga  4920
gcttgagaag gatttacttc atcttaaaga gtttgtagaa aatactggaa tacaggaaaa  4980
aatccagatg aatatagata acccaccaaa acacctgcag ggcactgagg tactaatata  5040
caagatcaga gagttgacta agttgtatca agtgtgctat gattatgtta agtcaacaga  5100
acacaaagtg aaagttttca tcctgccatat gaaatcatac acatccatag aatttttgtac  5160
attaatacag ggaaacacta taagtgacag taagtggtac acaatgcact atttgaagca  5220
ggtcttaggg ggaactatga aaggtcatat gatgaccact agtactagcg aacaggttat  5280
agctgcagaa tgttttaggg tcttgacgca ttttgctgat gcatttgtag aagaaggaag  5340
tagggttagc ttcttaaatg aaatattgga taaattcaca tataaaaatg ttagtgtcaa  5400
```

```
ttacttatta aatgtactac tggcaagttc taatagatta gactttatac cattgctctt    5460
ccggactaag atgttgacgc agcaggatct taataaattt gatgcattga aaacaaacga    5520
aagagtatca tggaataact ggcaaacaaa tagaggcctg aactctggga tcatagacct    5580
gacaatatct ggatacctga ggtctatccg tatcgtagga gaagataata aattgaaaat    5640
tgcagaacta acaattccaa atttcttacc gaatactata ttccatgctg gcaataagtt    5700
gttgaactct aggcataatc taaagtttga gtatatggag gaatatgttt tagatgataa    5760
atacaattat tatattactt atcagaaaaa gagagctaat ctatatacct accaggtttc    5820
cacagttgat cacatatgga ggagaaatga ggaaggcaat caaaaacgtg gcaaacgata    5880
caataagatg gtgccagttt gtccagtagt tgttagttca agagatgaga tgtttaagat    5940
atcaatgcaa aatgtgtttta gcttaaatct aacaaatttc aatctaacta aattgtttgt    6000
ttcaccagat gaagtagcaa ctataaaaaa agcacatatg tcaaagatga tgttcttctc    6060
aggtcctcag attaaagctg gcataattga cttgaccaca ttaatgagaa ctcaagagtt    6120
actcacatta aattatgaca atctttgtaa gtcaagcata ataccttttct gtagaattct    6180
tgcatgtaat ggagaagaac ctggagagtt aattttccta tctgatgaag tgatggaatt    6240
cactatttct gaagaaattg agtcaatgcc tatattcacc atcagatacc agaagagagg    6300
taacagttca atgacataca agaatgcaat aagaacattg gtcgcaaatg tgtagatga     6360
aattaaggag gtctttgatt tttcaggtga gggattctat tctaagaaaa atctaggaat    6420
tataaataca atttgttcca caatcgaagt gttggaaaca aatgagtggt ccactatatt    6480
actcaattct ttccatatag ccatgctctt agaaaatatg gacagagaat tccacttatt    6540
ttcaatgcct ggtgctttct tctctaatgt ggctaatggc accatcaact ggacaaaact    6600
attaaaattt gttaagtctt tgccagcagt aaagaaagag ccatggtcta tgatgatgga    6660
aagattcatt gagaaaaactg tatacttgat agaaaagaga atcaacaaag aagtagattt    6720
taatgacttt ttagaggaat tggaataccca atcaggaaag tctatgttca cattcttctg    6780
accacaccaa tcaggctatc taccaaacca caaatatat atatgaatat atacacacaa      6840
gtgtgtatat atacatatat atatacaaaa aaacagcaga gcaatagagc agtgattata    6900
ttttcagaca ccaaaatttg caaaaaata caatttttat atataggagc acactactgg     6960
gtcggcatgg                                                           6970
```

```
SEQ ID NO: 15           moltype = DNA   length = 4591
FEATURE                 Location/Qualifiers
source                  1..4591
                        mol_type = other DNA
                        organism = synthetic construct
SEQUENCE: 15
atacgactca ctatagagta gtgtactacc gatatacaca aaccaatcgt tcgtttatta     60
ttgtttttaa gatggcgatt tctattgtct tgatgatcat cttctcaacc acctcttgcc    120
tagcaagagc agcaccatca atatcaaaat gtttccaaga tggagtgctg atagcagaga    180
agaagagctc atcaggaata tcagagttct gcattaaaga tgatatttcc atactaaagt    240
cagagataaa ttattcaaaa aatgacacag ggatatcat gcatagcaaa gttttcaggc    300
attggacagt agcagattgg aagcaatgtc aacccattcc atctgcaggt ggcagcataa    360
atgtcttgga agttgacaaa atctaaaacc ttgttgctaa aaattatatg tgtactagac    420
cttgtgtcat aaccattgac aaggagaatg cgcaattact gttcagaca gaacaactga    480
accagttgga ggttacggga acaacaatca gcacaggttg gtttaaatca aaaacttctg    540
tgtcccttga caacacatgt gaacatatta aagtgacttg tggcaaaaaa agcttgcaat    600
tccatgcttg ctttaagcaa catatgtcat gcgttaggtt cttgcacaga agtgttctgc    660
caggttacat ggcaaattca atatgccaaa acatagaact cattataatc atcacattaa    720
cctagctat tttcatattc atgtgtataa taacaaggac atacattttgt tacatcatgc    780
tgccctgtt tgcccaata gcttatatat atggatggtt atataaccgc agttgtaaga    840
aatgtatatg ttgcggatta gcatatcatc ctttcacaaa ttgtgggtcc tactgtgttt    900
gtggttcccg ctttgaaaca tcagatcgca tgcgccttca tagagaatct ggcttgtgtc    960
agggcttcaa atcacttaga gtagcaagga cactatgcaa gtcaaaggga tcatctttag    1020
ttatatcagt gctaactgca atgcttatac tttcatttgt cacacccctt gaagctatct    1080
caacaaatta ccccacagat aggaagtata cactaaatga ggtgaatgat atagtccttg    1140
ggaaagggac ggaaaatgag ctgaagacat caatattggc attagtgtcc atttgcggta    1200
tagggatcat tatcatattt atagcattga caatgcttttt agacattgtg ttggaagcta    1260
tagctaaaag gagcacaata ttttgcacag aatgcaactt aatacatgac aaaaaggcaa    1320
tgaaatttgt cggagatttc acaaacaaat gtgggttttg cccatgtggt gaattagaag    1380
acccagaggg gctagttata catacaacaa gaaagtcttg tacatattat attaaaatta    1440
gaaacctcaa gctaattatg cttgtgtttt caattgccat ttaatgcaa aatacagcaa    1500
tgcttgtcgt tgctgatgag aattgctgga cgaacacaga aatcaaggca gactgtgttg    1560
ggccattgat tgggcccaca acgtgcacta taaagggtc aaaaacatac aaggcagtgg    1620
cacaagagct ggttacatca aacaagataa cacaattgga tgctgacaag tacacattat    1680
taggtgacac aatagagagt gcactgagtg ctataacaga gcaaaaacat tattctgcaa    1740
tacatctact agagacaatt ttcctgatga aacactgtga ttattataac gttttatgaac    1800
ataatagtgg gtattcccaa acaaagtgga ggctaattgc caagacaaat agttttgaca    1860
tctgctctat accatctaca ccaaattttt gcaaatgctt gtcagattcc agctgctcca    1920
caagtacttt gaactttgca acgtcaatga actctactta cactagcaaa gcagaatact    1980
ttaatcatga ctttactttg tttttaaata tatttgaggc tgcattccca gggagtgcca    2040
cagcattctt attcaagaaa ataaaagaaa aagctcctca tcaggctttt gaaatgatgg    2100
gtaaaattgc taataagtac ccaaataata gttattggt agtgttgcta aaatatggtc    2160
agtatatggt tggtctaagt catgcttcaa cttatcagct caagcaagaa tggattgcta    2220
aatcgctaag cttagtgagg tcaacaaaaa caggccttaa gatggcaatg acaaatcag     2280
agcctggccc tgccactaag gaatgttcag atgcaaaaac tattgcatgc ctgactccca    2340
aattccaggt agaggttaac aacctcatga gttgctgata tttaaaatat                2400
atatgaagag cggagagctc tacaaggctc atgataggaa ctcagtgtgg tgcctaaatg    2460
atatgcattg cctaacacca tatccccag caaatgctga gctgttgca acaatgaaga    2520
agatggaatg ctggcaagac aatcctaaac aacctacaaa tgattatgca acaccaagaa    2580
gaagctgtca aatgaaggac aggggttat gcaacgtagg agccgataag tggaaagtta    2640
taaaatgtga tgatgatttg atgttttaca cagatgcact agagagtcca gatccagctg    2700
```

```
cagacatagg gcaatattgc ttctcagaaa aatgccaaat agaaagatac ccaataaatc   2760
caactagctt aacaaattgt gaatggttgt atagagctgt gaagcctcaa tatataaaaa   2820
ggctgtcatt acagacaata gaagaatata agaaagcaat tactgacaaa ttgacacaca   2880
ctctgcagtt gtatcatttt gcaccactag aaaacttgcc acatattagg cctacatatg   2940
agtacattac agcacagggc acttacacag cagatggcat agaaggtgca agtataataa   3000
catcaatacc agcattgagt ggaacaagtg tgggatttaa aataaatgca aaagatggga   3060
cagcactcct tgatatagtt gtgtacatta agtcatctgt ggtgaaaagt gtttataatc   3120
acatttatga tacagggcct actattaaca taaactcaaa acatgatgaa ttgtgcactg   3180
gacaatgtcc aaaaagaata cctgcagacc caaactggct cacattttcc caggaaagaa   3240
ctagtaggtg gggctgcgaa gaatttgggt gtttagcaat aaacacaggt tgtgtatatg   3300
gttcctgtca agatgtaatc agaacagaaa caaaggttta taggaaagca aatgaggaaa   3360
cagtgatgtt gactgtttgt ataacatacc cagggcatac gttctgcaca gatgtgaatg   3420
cactagagcc caagataacc gatgaattgg aactccaatt taaaacaata gacataaaaa   3480
gtttaccaaa tttagtggct ataactaatc ataaattgta tacagggcaa ataaatgatc   3540
ttggaacctt tggccaaatg tgtgggaatg tccaaaagac aaaacacaagt atactgggtg   3600
caggcacccc aaaattcgat tacacctgtt atagcgccag tagaaaagat ataataattc   3660
gcagatgcta caataacaat tatgactctt gtaggcttct aaaacaggaa ggggatctct   3720
tgtttgatga caaccatgag acattgatag tgtataacaa caaaaggctg aatggagaac   3780
tgacaatgaa gttgctcctt ggagatatac aatacaagct ctacacagaa aacatggagc   3840
ttgagctgga agcaaaatgt gttggatgtg taggctgctt tgagagctac cagtgtaact   3900
tacaaatcac atccagctta gatgggaatt gtgccatatc aggaccctgt gagaccttcc   3960
atgacaggat ccagataaaa acgacaaaaa aagactagct attaaagcta gcttgtacaa   4020
aggatcctgg cgataaggcc acatttagag tatgtggtaa agactatgat ttcaacttcc   4080
acacagttgt aaaaaatgac aaaattgaag tcaatgttgg ggatgaaact tcatatatca   4140
aagaaaagga tgctagatgt ggaacatggc tatgtagggt gagagatgaa ggtctaagtg   4200
taatctttga gcctctgaaa aacttcttt gcaattattt gaatatgttc ctctacatac   4260
ttggaggagt tctttactg tttttatcac tttatattat aatgccagta tgtgcgagac   4320
taagagatga attaaagaag aatgaaaaat tacaccagat ggagatgaag aaaagataaa   4380
aaccatgcct aaaatgatgc accgctgttg tataaattaa gctattagat aataaattaa   4440
aatataatga aaaataacac aaaaaaagaa gaaatcccct tagcagcttt taaattgcta   4500
attttaatat gctgctttga gatgtttaaa atgcaaatta atatattatt ttgtgtttgc   4560
ttttatcggt agcacactac tgggtcggca t                                  4591

SEQ ID NO: 16       moltype = DNA  length = 1002
FEATURE             Location/Qualifiers
source              1..1002
                    mol_type = other DNA
                    organism = synthetic construct
SEQUENCE: 16
acgactcact atagagtagt gtactccacg cataaaactt tttatcgttg agacattact    60
actagaggat ttgagtcttt gacttattct ttcttttca atgttggagc tagaatttga   120
agatgtccct actaacatcg ggagtacttt tgaccctgaa tcaggataca ttaactttca   180
gcgtaactac ctgccagggg ttacgcttga ccaaattcgt atcttctaca ttaaaggacg   240
cgagattaaa aatagtctcg caaaagaag tgaatgggaa gttacgctta atcttgggg    300
ctggaaggtg cctgtactca atacgaattt ccctggaaac aggagcaatg cagtgcctga   360
ctacggtctt accttccacc gcatcagcgg ataccttgcc aggtacttac ttggaaaata   420
ccttgcagaa actgaaccag aaaagctcat aatgagaaca aaaatcatca accctcttgc   480
tgagaaaaat ggcatcacct gggaaagtgg accagaggtt tatctctcat tcttccctgg   540
tgcagagatg ttccttggaa cttttcaagtt ctatccactt gccattggaa tctacaaagt   600
gcagaggaaa gagatggacc caaaattcct ggaaaagaca atgcgccaga ggtacctcgg   660
ccttgatgct cagacatgga caacaactaa gcttgatgtg gtggagagag ccctaaaagt   720
ggtctcaggg cttggctgga gaaaaaccaa tgtcagcaat gctgcaaggg aattcctgtc   780
taagtttgga atcagaatgt aaggattcag aaagagaaaa taattcggcc aaatttcatt   840
atattaattc gaccaaaaag gggttttta ccccaaacaa tcaaagcagc attgcagatg    900
ggtgggtggt tggggacagt aactgactac aacattaatt taacatttca ctttatttga   960
tattgtttaa gtttaaggtg gagcacacta ctgggtcggc at                     1002

SEQ ID NO: 17       moltype = DNA  length = 768
FEATURE             Location/Qualifiers
source              1..768
                    mol_type = other DNA
                    organism = synthetic construct
SEQUENCE: 17
cttttttcaat ggtgagcaag ggcgaggagc tgttcaccgg ggtggtgccc atcctggtcg    60
agctggacgg cgacgtaaac ggccacaagt tcagcgtgtc cggcgagggc gagggcgatg   120
ccacctacgg caagctgacc ctgaagttca tctgcaccac cggcaagctg cccgtgccct   180
ggcccaccct cgtgaccacc ctgacctacg gcgtgcagtg cttcagccgc taccccgacc   240
acatgaagca gcacgacttc ttcaagtccg ccatgcccga aggctacgtc caggagcgca   300
ccatcttctt caaggacgac ggcaactaca agacccgcgc cgaggtgaag ttcgagggcg   360
acaccctggt gaaccgcatc gagctgaagg gcatcgactt caaggaggac ggcaacatcc   420
tggggcacaa gctggagtac aactacaaca gccacaacgt ctatatcatg gccgacaagc   480
agaagaacgg catcaaggtg aacttcaaga tccgccacaa catcgaggac ggcagcgtgc   540
agctcgccga ccactaccag cagaacaccc ccatcggcga cggccccgtg ctgctgcccg   600
acaaccacta cctgagcacc cagtccgccc tgagcaaaga cccccaacgag aagcgcgatc   660
acatggtcct gctggagttc gtgaccgccg ccgggatcac tctcggcatg gacgagctgt   720
acaagggaag cggagctact aacttcagcc tgctgaagca ggctggag                768

SEQ ID NO: 18       moltype = DNA  length = 9237
FEATURE             Location/Qualifiers
```

```
source                  1..9237
                        mol_type = other DNA
                        organism = synthetic construct
SEQUENCE: 18
ggaagcggaa gagcgcccaa tacgcaaacc gcctctcccc gcgcgttggc cgattcatta   60
atgcagggg  atctcgatcc cgcgaaatta atacgactca ctatagagta gtgtactcct  120
atatataaaa attaaaaata tcaaattgtt ctgaacatgg aggatccaat gtatgagcag  180
ttcttacaaa ggatccaagc agtcagaaca gctactgtgg ctaaggacat cagtgctgac  240
atactggagg caagacatga ttactttggg cgagagctct gccgagcatt ggacattgag  300
tatagaaaca atgttttgct tgatgagata atattggacg tttatccagg agttaacctt  360
atggagtata atgttccaca tgttacccct gataattata tctggactgg ggatatgttg  420
ctgatattag actacaaagt ctctgttggg catgatagta ctgaagtgac atacaaaaaa  480
tatacaacac taatcctccc agtcatgcaa gaaattggta taaacacaga aatttgcatt  540
ataagggcaa atccagttac aaatcaaata agcattgttg gtgacaatt  taaacgattg  600
tttccaacaa ttcctgtcga gctcaatttt gcaagatttt ttgaactaag aaaaatgctc  660
ttagatataaa ttgctgatga tgaagaattt taatgatga  tagctcatgg tgactttacc  720
ttgactgcac cttggtgcca ggatgactat cctgaactaa tagaccatcc tatataccaa  780
gagtttcttg gctctatgcc cccacgattt gtatcaatgt ttgaagaagc catgacttt   840
agtgcataca atgcggagcg ctggaataca ctactatata aaataaaaaa cttgactctt  900
gaggattacc aagattattt gaatataaag tcccacaaca tatttaatat gacaggagat  960
tttatgaagc cgactcaaga tgaaatagat attggctggg aatccatgag taagagaata 1020
tcacaagaga gagagttgac cacagatata aataaacaaa aaccttcaat acatttcatc 1080
tgggcgcaaa ataagatag  gaagttgtta aattccacag caaaactggt gttcctatca  1140
aacaccttac agagtataac agaacaatca acctggacag atgctttaaa ggctataggt 1200
gttagtatgt atattggtaa taatattgga ttgtatgaaa atttatgtgc tgagagaaag 1260
ctaattgcac gatcaaccgg taaaaaggtt aataataaga gattagaagc tgtcaaaatc 1320
gggaaagccc ttgtattgtg ggaacaacag ttcattcttg ctaatgaatt attcaaagga 1380
caagaaagac aaaagtttat aaaaaacttt tttggtatag gtaagcacaa aaccttcaaa 1440
gataaaacat cagaagatct tgatagagaa aagccaaaaa ttttagattt taataacact 1500
agagtactaa tggctgcaag gactatggta aacaaaaata aaaaatttct tagtcaagat 1560
aatacactag agtttgatca cccaattata tcaacttact ttgatcaagt aagggaggca 1620
tccatagata ctgccaagt  actgaagaag atctccaaga catgttttg  gcaagccata 1680
acagacatat ctacattaat gaggaacatc ttagcagtct ctcaatacaa tagacacaat 1740
acattccgcg tggcaatgtg tgcgaatgat tcaatatatg tcttgtgtt  tccttcttca 1800
gacattaaaa caaagagagc tacaattgtc ttctgcattg tctgtatgca taattctaga 1860
gatgacatta tggatgcagg tgcactattt accactttgg aaaccaaaac taaaacattt 1920
gtgtctataa gtaaggcaat tagattggat aaggaaagat gtcagagaat tgtctcatct 1980
cctggcctat ttattctcag cacactatta ttatacaata acaatactga aatatcata  2040
tatgatgtca tgaattttac attctacact agcttgtcaa tacaaaaag  catgctatct 2100
ctaacagaac catctagata tatgataatg aattcacttg caatatctag tcatgttaga 2160
gattatatag cagaaaaatt ttctccgtac acaaaaactt tgttcagtgt ttatatggtt 2220
aacttgatca agagaggctg tgccactgcc aatgagcaat ctgagaagat ccaagtcaga 2280
aatatatatc tatcagatta tgatataacg caaaagggaa taatgacat  tagaaattta 2340
gactcgatat ggttccccgg caaagttaat ttgaaggaat acataaatca aatctatcta 2400
ccattttatt tcaatgcaaa gggactacat gaaaaacatc atgttatgat tgacttagca 2460
aagactgttt tagaaataga aatgaatcaa aggttagacc aattaggaat ttggtctaag 2520
aatgaaaaaa aacaacatgt caatctgcca attttggttc attcaattgc taagtcattg 2580
atattagaca catccagaca caaccatctg aggaatagag ttgagagcag aaataatttt 2640
aggaggagca tctcaaccat cagcactttt acaagctcaa aatcttgtat aaaaataggc 2700
gaattccaag atctgaaaac aaaagaattt aaagcaacta aaaaaatgaa tgagaagata 2760
aatcagaaat ttagattagc caatccattg ttcattgatg ataaggatgc tgcagaa    2820
ataatgcatt gtaattatga tcagctgaaa acaaaagtac cgaattataa ggattatatc 2880
tcagttaagg tctttgatag attatatgag ctttacaaaa caaggagct  tgatgacaaa 2940
ccatttatag aacaagcaat gaagatgatg aaagagcata agaattcaa  tttcacattc 3000
tttaataagg gacaaaaaac atctaaggac agggaaatat ttgttgggga gtttgaagca 3060
aaaatgtgca tgtatgttgt tgaacgaatt tccaaagaaa gatgcaagct gaatgaagat 3120
gaaatgatca gtgagcctgg ggataccaaa ctgagaatat tagaaaaaaa agcagaagag 3180
gagatcagat atatagttga aaaaactaaa gatagtattt tgaaggaga  ccctgcacat 3240
gcattaaaat tagaaattaa tgcagatatg tcaaaatgga gtgcacaaga tgttttcttc 3300
aagtatttct ggttggtagc aatggatcct atactgtacc catcggaaaa gaagaggatt 3360
ttatatttca tgtgcaatta tatgcagaaa aatttgatcc ttccggacga cttattatcc 3420
aatataatga atcagaggag accatatgag aatgatataa tactagaatc aaccaatgga 3480
ttggcacaga actttgtgca aattaaaaga aactggcttc aaggtaattt caattatatg 3540
tcaagctatg ttcatagctg tgctatgtta gtatacaaga atgttgccaa agaggctgta 3600
aaactgcttg atggcaattg tttagtgaat tctatggtgc actctgacga taaccaaaca 3660
tcattgtcca tcattcaaaa caaattaaag gataatatga tcatagaata tgtggcaaaa 3720
ctatttgaag cagtttgctt ggcatttggt tgccaagcca acatgaagaa aacctatatc 3780
acccacacat gcaaagagtt tgtctcactg ttcaatttgc atggtgagc  tttatcaata 3840
tatggcaggt tcttactacc aagtgttgga gattgtgcat ataggtcc   ctatgaagat 3900
ttagcaagta ggctgtccgc cgcacaacaa agcttaaaac atggttgtcc tccaagttat 3960
gtctgggttg ccattagttg tagccattgg ataacgcatt tcacttacaa tatgatgcat 4020
gatcaagtca actctcccat gcagtatcta ccgtttgaag atagattcca agtcccaact 4080
gaattgaatg gttatttatc tgcaccatta tatcttattg cattaatagg aatagaggct 4140
gacaatttat ggttcctgtt aaacatattg aagaaactag ccattaga   acagaaag   4200
gaaacaatac aaacacaatt cactgctatt caagataata taaacaaatt gacaccttct 4260
gagttatttta gattaaagtt gctaagatat ctgacattgg acacagagat aacatcgac  4320
tccaacatgg gagagacaag tgatatgagg agtaggtctt tattaacacc aaggaaattc 4380
acaactgcag gctcactaaa taattggta  tcctacaatg atttcaagaa tgctatgaat 4440
acaaatgaat tcaagagaa  cttagaatat atggaaatga tccagaact  tcttgtcaca 4500
```

```
aaaggcgaaa ataaagaaca atatataaac tccatcttat ttagatataa ctcaaagaga    4560
tttaaagaaa gcttatcaat acaagcacct tcacaactct ttgttgagca gatactattt    4620
tcccataagc ctattattga ttatagtagt atctttgaca aactagcatc tatggcagag    4680
acagaaataa tagagaactt accagacatt attggtagag tcacctaccc tcaggcatat    4740
caaatgataa cgagagatat aacacaatta cctctgacta ttgatgacat aaagatcgta    4800
ttcaagtatt gtgtattaaa tgacccatta attatcactg ctgctaatac atccttgctc    4860
tgtgtgagag gtgcgccaca agatagaact ggattaagtg catgccaaat gccagaattc    4920
cgtaatatga aactcataca tcattcacca gcactagttc tcaaggcatt tagtaagggg    4980
acagtagata tacctggtgc agaccctgta gagcttgaga aggatttact tcatcttaaa    5040
gagtttgtag aaaatactgg aatacaggaa aaaatccaga tgaatataga taacccacca    5100
aaacacctgc agggcactga ggtactaata tacaagatca gagagttgac taagttgtat    5160
caagtgtgct atgattatgt taagtcaaca gaacacaaag tgaaagtttt catcctgcct    5220
atgaaatcat acacatccat agaatttgt acattaatac agggaaacac tataagtgac    5280
agtaagtggt acacaatgca ctatttgaag caggtcttga gggaactat gaaaggtcat    5340
atgatgacca ctagtactag cgaacaggtt atagctgcag aatgttttag ggtcttgacg    5400
cattttgctg atgcatttgt agaagaagga agtagggtta gcttcttaaa tgaaatattg    5460
gataaattca catataaaaa tgttagtgtc aattacttat taaatgtact actggcaagt    5520
tctaatagat tagactttat accattgctc ttccggacta agatgttgac gcagcaggat    5580
cttaataaat ttgatgcatt gaaaacaaac gaaagagtat catggaataa ctggcaaaca    5640
aatagaggcc tgaactctgg gatcatagac ctgacaatat ctggatacct gaggtctatc    5700
cgtatcgtag gagaagataa taaattgaaa attgcagaac taacaattcc aaatttctta    5760
ccgaatacta tattccatgc tggcaataag ttgttgaact ctaggcataa tctaaagttt    5820
gagtatatgg aggaatatgt tttagatgat aaatacaatt attatattac ttatcagaaa    5880
aagagagcta atctatatac ctaccaggtt tccacagttg atcacatatg gaggagaaat    5940
gaggaaggca atcaaaaacg tggcaaacga tacaataaga tggtgccagt ttgtccagta    6000
gttgttattc caagagatga gatgtttaag atatcaatgc aaaatgtgtt tagcttaaat    6060
ctaacaaatt tcaatctaac taaattgttt gtttcaccag atgaagtagc aactataaaa    6120
aaagcacata tgtcaaagat gatgttcttc tcaggtcctc agattaaagc tggcataatt    6180
gacttgacca cattaatgag aactcaagag ttactcacat taaattatga caatctttgt    6240
aagtcaagca taatacccttt ctgtagaatt cttgcatgta attggagaaga acctggagag    6300
ttaattttcc tatctgatga agtgatggaa ttcactattt ctgaagaaat tgagtcaatg    6360
cctatattca ccatcagata ccagaagaga ggtaacagtt caatgacata caagaatgca    6420
ataagaacat tggtcgcaaa tggtgtagat gaaattaagg aggtctttga tttttcaggt    6480
gagggattct attctaagaa aaatctagga attataaata caatttgttc cacaatcgaa    6540
gtgttggaaa caaatgagtg gtccactata ttactcaatt cttcctcatat agccatgctc    6600
ttagaaaata tggacagaga attccactta ttttcaatgc ctggtgcttt cttctctaat    6660
gtggctaatg gcaccatcaa ctggacaaaa ctattaaaat ttgttaagtc tttgccagca    6720
gtaaagaaag agccatggtc tatgatgatg aaagattca ttgagaaaac tgtatacttg    6780
atagaaagag agatcaacaa agaagtagat tttaatgact ttttagagga attggaatac    6840
caatcaggaa agtctatgtt cacattcttc tgaccacacc aatcaggcta tctaccaaac    6900
cacaaaatat atatatgaat atacacac aagtgtgtat atatacatat atatatacaa    6960
aaaaacagca gagcaataga gcagtgatta tattttcaga caccaaaatt tgcaaaaaaa    7020
tacaatttt atatatagga gcacactact gggtcggcat ggcatctcca cctcctgcg    7080
gtccgacctg gcatccgaa ggaggacgtc gtccactcgg atggctaagg gagagctcgg    7140
atccggctgc taacaaagcc cgaaaggaag ctgagttggc tgctgccacc gctgagcaat    7200
aactagcata accccttggg gcctctaaac gggtcttgag gggttttttg ctgaaaggag    7260
gaactatatg acgaattctc tagatatcgc tcaatactga ccatttaaat catcctgac    7320
ctccatagca gaaagtcaaa agcctccgac cggaggcttt tgacttgatc ggcacgtaag    7380
aggttccaac tttcaccata atgaaataag atcactaccg ggcgtatttt ttgagttatc    7440
gagattttca ggagctatga gccatattca acgggaaacg tcttgctcga ggccgcgatt    7500
aaattccaac atggatgctg atttatatgg gtataaatgg gctcgcgata atgtcgggca    7560
atcaggtgcg acaatctatc gattgtatgg gaagcccgat gcgccagagt tgtttctgaa    7620
acatggcaaa ggtagcgttg ccaatgatgt tacagatgag atggtcaggc taaactggct    7680
gacggaattt atgcctcttc cgaccatcaa gcatttatc cgtactcctg atgatgcatg    7740
gttactcacc actgcgatcc cagggaaaac agcattccag gtattagaag aatatcctga    7800
ttcaggtgaa aatattgttg atgcgctggc agtgttcctg cgccggttgc attcgattcc    7860
tgtttgtaat tgtccttta acggcgatcg cgtatttcgt ctcgctcagg cgcaatcacg    7920
aatgaataac ggtttggttg gtgcgagtga ttttgatgac gagcgtaatg ctggcctgt    7980
tgaacaagtc tggaaagaaa tgcataagct tttgccattc tcaccggatt cagtcgtcac    8040
tcatggtgat ttctcacttg ataaccttat ttttgacgag gggaaattaa taggttgtat    8100
tgatgttgga cgagtcggaa tcgcagaccg ataccaggat cttgccatcc tatggaactg    8160
cctcggtgag ttttctcctt cattacagaa acggcttttt caaaaatatg gtattgataa    8220
tcctgatatg aataaattgc agtttcactt gatgctcgat gagtttttct aaatgaccaa    8280
acaggaaaaa accgccctta acatggcccg ctttatcaga agccagacat taacgcttct    8340
ggagaaactc aacgagctgg acgcggatga acaggcagac atctgtgaat cgcttcacga    8400
ccacgctgat gagctttacc gcagctgcct cgcgcgtttc ggtgatgacg gtgaaaacct    8460
ctgatgaggc ccaaatgta atcacctggc tcaccttcgg gtgggccttt ctgcgttgct    8520
ggcgtttttc cataggctcc gccccctga cgagcatcac aaaaatcgac gctcaagtca    8580
gaggtggcga aacccgacag gactataaag ataccaggcg tttccccctg gaagctccct    8640
cgtgcgctct cctgttccga ccctgccgct taccggatac ctgtccgcct ttctcccttc    8700
gggaagcgtg gcgctttctc atagctcacg ctgtaggtat ctcagttcgg tgtaggtcgt    8760
tcgctccaag ctgggctgtg tgcacgaacc ccccgttcag cccgaccgct gcgccttatc    8820
cggtaactat cgtcttgagt ccaacccggt aagacacgac ttatcgccac tggcagcagc    8880
cactggtaac aggattagca gagcgaggta tgtaggcggt gctacagagt tcttgaagtg    8940
gtggcctaac tacggctaca ctagaagaac agtatttggt atctgcgctc tgctgaagcc    9000
agttacctcg gaaaaagagt tggtagctct tgatccggca aacaaaccac cgctggtagc    9060
ggtggttttt tgtttgcaa gcagcagatt acgcgcagaa aaaaggatc tcaagaagat    9120
cctttgattt tctaccgaag aaaggcccac cgtgaaggt gagccagtga ttgattgca    9180
gtccagttac gctggagtct gaggctcgtc ctgaatgata tcaagcttga attcgtt    9237
```

```
SEQ ID NO: 19         moltype = DNA   length = 6858
FEATURE               Location/Qualifiers
source                1..6858
                      mol_type = other DNA
                      organism = synthetic construct
SEQUENCE: 19
ggaagcggaa gagcgcccaa tacgcaaacc gcctctcccc gcgcgttggc cgattcatta    60
atgcaggggg atctcgatcc cgcgaaatta atacgactca ctatagagta gtgtactacc   120
gatatacaca aaccaatcgt tcgtttatta ttgttttaa dgatggcgatt tctattgtct   180
tgatgatcat cttctcaacc acctcttgcc tagcaagagc agcaccatca atatcaaaat   240
gtttccaaga tggagtgctg atagcagaga agaagagctc atcaggaata tcagagttct   300
gcattaaaga tgatatttcc atactaaagt cagagataaa ttattcaaaa aatgcacag    360
ggatattcat gcatagcaaa gttttcaggc attggacagt agcagattgg aagcaatgtc   420
aacccattcc atctgcaggt ggcagcataa atgtcttgga agttgacaaa atctaaacc    480
ttgttgctaa aaattatatg tgtactagac cttgtgtcat aaccattgac aaggagaatg   540
cgcaattact gtttcagaca gaacaactga accagtttga ggttacggga caacaatca    600
gcacaggttg gtttaaatca aaaacttctg tgtcccttga caacacatgt gaacatatta   660
aagtgacttg tggcaaaaaa agcttgcaat tccatgcttg ctttaagcaa catatgtcat   720
gcgttaggtt cttgcacaga agtgttctgc caggttacat ggcaaattca atatgccaaa   780
acatagaact cattataatc atcacattaa ccttagctat tttcatattc atgtgtataa   840
taacaaggac atacatttgt tacatcatgc tgccccttgt tgccccaata gctatataat   900
atggatggtt ataaccgc agttgtaaga aatgtatatg ttgcggatta gcatatcatc    960
ctttcacaaa ttgtgggtcc tactgtgttt gtggttcccg ctttgaaaca tcagatcgca  1020
tgcgccttca tagagaatct ggcttgtgtc agggcttcaa atcacttaga gtagcaagga  1080
cactatgcaa gtcaaaggga tcatctttag ttatatcagt gctaactgca atgcttatac  1140
tttcatttgt cacacccctt gaagctatct caacaaatta ccccacagat aggaagtata  1200
cactaaatga ggtgaatgat atagtccttg ggaaagggac ggaaaatgag ctgaagacat  1260
caatattggc attagtgtcc atttgcggta tagggatcat tatcatattt atagcattga  1320
caatgctttt agacattgtg ttggaagcta tagctaaaag gagcacaata ttttgcacag  1380
aatgcaactt aatacatgac aaaaaggcaa tgaatttgt cggagatttc acaaacaaat  1440
gtgggttttg cccatgtggt gaattagaag acccagaggg gctagttata catacaacaa  1500
gaaagtcttg tacatattat attaaaatta gaaacctcaa gctaattatg cttgtgtttt  1560
caattgccat tttaatgcaa aatacagcaa tgcttgtcgt tgctgatgag aattgctgga  1620
cgaacacaga aatcaaggca gactgtgttg ggcattgat tgggcccaca acgtgcacta  1680
ataaagggtc aaaaacatac aaggcagtgg cacaagagct ggttacatca aacaagataa  1740
cacaattgga tgctgacaag tacacattat taggtgacac aatagagagt gcactgagtg  1800
ctataacaga gcaaaaacat tattctgcaa tacatctact agagacaatt ttcctgatga  1860
aacactgtga ttattataaa gtttatgaac ataatagtgg gtattcccaa acaaagtgga  1920
ggctaattgc caagacaaat agttttgaca tctgctctat accatctaca ccaaattttt  1980
gcaaatgctt gtcagattcc agctgctcca caagtacttt gaactttgca acgtcaatga  2040
actctactta cactagcaaa gcagaatact ttaatcatga ctttactttg tttttaaata  2100
tatttgaggc tgcattccca gggagtgcca cagcattctt attcaagaaa ataaaagaaa  2160
aagctcctta tcaggctttt gaaatgatgg gtaaaattgc taataagtac ccaaataata  2220
agttattggt agtgttgcta aaatatggtc agtatatggt tggtcaagt catgcttcaa  2280
cttatcagct caagcaagaa tggattgcta aatcgctaag cttagtgagg tcaacaaaaa  2340
caggccttaa gatggcaatg acaaatgcag agcctgccc tgccactaag gaatgttcag  2400
atgcaaaaac tattgcatgc ctgactccca aattccaggt agaggttaac aacctcatga  2460
gttgtggtgc ttcccctaat ttaaaatat atatgaagag cggagagctc tacaaggctc  2520
atgataggaa ctcagtgtgg tgcctaaatg atatgcattg cctaacacca tatacccag   2580
caaatgctga gcttgttgca acaatgaaga agatggaata ctggcaagac aatcctaaac  2640
aacctacaaa tgattatgca acaccaagaa gaagctgtca aatgaaggac aggggtttat  2700
gcaacgtagg agccgataag tggaaagtta taaatgtga tgatgatttg atgttttaca  2760
cagatgcact agagagtcca gatccagctg cagacatagg gcaatattgc ttctcagaaa  2820
atgccaaat agaaagatac ccaataaatc caactagctt aacaaattgt gaatggttgt  2880
atagagctgt gaagcctcaa tatataaaaa ggctgtcatt acagacaata gaagaatata  2940
agaaagcaat tactgacaaa ttgacacaca ctctgcagtt gtatcatttt gcaccactag  3000
aaaacttgcc acatattagg cctacatatg agtacattac agcacagggc acttacacag  3060
cagatggcat agaaggtgca agtataataa catcaatacc agcattggt ggaacaagtg   3120
tgggatttaa aataaatgca aagatggga cagcactcct tgatatagtt gtgtacatta  3180
agtcatctgt ggtgaaaagt gttatcaatc acatttatga tacagggcct actattaaca  3240
taaactcaaa acatgatgaa ttgtgcactg gacaatgtcc aaaaagaata cctgcagacc  3300
caaactggct cacattttcc caggaaagaa ctagtaggtg gggctgcgaa gaatttggt   3360
gtttagcaat aacacaggt tgtgtatatg gttcctgtca agatgtaata agaacagaaa  3420
caaaggttta taggaaagca aatgaggaaa cagtgatgtt gactgttgt ataacatacc   3480
cagggcatac gttctgcaca gatgtgaatg cactagagcc caagataacc gatgaattgg  3540
aactccaatt taaacaata gacataaaaa gtttaccaaa tttagtggct ataactaatc  3600
ataattgta tacagggcaa ataatgatc ttggaacctt tggccaaatg tgtgggaatg   3660
tccaaaagac aaacaccaagt atactgggtg caggcaccc aaaattcgat tacacctgts  3720
atagcgccag tagaaaagat ataataattc gcagatgcta caataacat tatgactctt   3780
gtaggcttct aaaacaggaa gggatctcc tgtttgatga caaccatgag acattgatag  3840
tgtataacaa caaaaggctg aatggagaac tgacaatgaa gttgctcctt ggagatatac  3900
aatacaagct ctacacagaa aacatggagc ttgagctgga agcaaatgt gttggatgtg  3960
taggctgtct tgaagctgac cagtgtaact tacaaatcac atccagctta gatgggttgt  4020
gtgccatatc aggaccctgt gagaccttcc atgacaggat ccagataaaa acgacaaaa   4080
aagactatgc attaaagcta gcttgtacaa aggatcctgg cgataaggcc acatttagag  4140
tatgtggtaa agactatgat ttcaacttcc acacagttgt aaaaaatgac aaaattgaag  4200
tcaatgtttgg ggatgaaact tcatatatca aagaaaagga tgctagatgt ggaacatggc  4260
tatgtaggggt gagagatgaa ggtctaagtg taatctttga gcctctgaaa aacttctttg  4320
```

```
gcaattattt gaatatgttc ctctacatac ttggaggagt tcttttactg ttttatcac   4380
tttatattat aatgccagta tgtgcgagac taagagatga attaaagaag aatgaaaaat   4440
tacaccagat ggagatgaag aaaagataaa aaccatgcct aaaatgatgc accgctgttg   4500
tataaattaa gctattagat aataaattaa aatataatga aaaataacac aaaaaaagaa   4560
gaaaatccct tagcagcttt taaattgcta attttaatat gctgctttga gatgtttaaa   4620
atgcaaatta atatattatt ttgtgtttgc ttttatcggt agcacactac tgggtcggca   4680
tggcatctcc acctcctcgc ggtccgacct gggcatccga aggaggacgt cgtccactcg   4740
gatggctaag ggagagctcg gatccggctg ctaacaaagc ccgaaaggaa gctgagttgg   4800
ctgctgccac cgctgagcaa taactagcat aaccccttgg ggcctctaaa cgggtcttga   4860
ggggttttt gctgaaagga ggaactatat gacgaattct ctagatatcg ctcaatactg   4920
accatttaaa tcatacctga cctccatagc agaaagtcaa aagcctccga ccggaggctt   4980
ttgacttgat cggcacgtaa gaggttccaa ctttcaccat aatgaaataa gatcactacc   5040
gggcgtattt tttgagttat cgagattttc aggagctatg agccatattc aacgggaaac   5100
gtcttgctcg aggccgcgat taaattccaa catggatgct gatttatatg ggtataaatg   5160
ggctcgcgat aatgtcgggc aatcaggtgc gacaatctat cgattgtatg ggaagcccga   5220
tgcgccagag ttgtttctga aacatggcaa aggtagcgtt gccaatgatg ttacagatga   5280
gatggtcagg ctaaactggc tgacggaatt tatgcctctt ccgaccatca agcatttat    5340
ccgtactcct gatgatgcat ggttactcac cactgcgatc ccagggaaaa cagcattcca   5400
ggtattagaa gaatatcctg attcaggtga aatatattgt tgatgcgctgg cagtgttcct   5460
gcgccggttg cattcgattc ctgtttgtaa ttgtcctttt aacggcgatc gcgtatttcg   5520
tctcgctcag gcgcaatcac gaatgaataa cggtttggtt ggtgcgagtg attttgatga   5580
cgagcgtaat ggctggcctg ttgaacaagt ctggaaagaa atgcataagc ttttgccatt   5640
ctcaccggat tcagtcgtca ctcatggtga tttctcactt gataaccta ttttttgacga   5700
ggggaaatta ataggttgta ttgatgttgg acgagtcgga atcgcagacc gataccagga   5760
tcttgccatc ctatgaact gcctcggtga gttttctcct tcattacaga aacggctttt   5820
tcaaaaatat ggtattgata atcctgatat gaataaattg cagtttcact tgatgctcga   5880
tgagttttc taaatgacca aacaggaaaa aaccgccctt aacatggccc gctttatcag   5940
aagccagaca ttaacgcttc tggagaaact caacgagctg gacgcggatg aacaggcaga   6000
catctgtgaa tcgcttcacg accacgctga tgagctttac cgcagctgcc tcgcgcgttt   6060
cggtgatgac ggtgaaaacc tctgatgagg cccaaatgt aatcacctgg ctcaccttcg    6120
ggtgggcctt tctgcgttgc tggcgttttt ccataggctc cgcccccctg acgagcatca   6180
caaaaatcga tgctcaagtc agaggtggcg aaacccgaca ggactataaa gataccaggc   6240
gtttcccct ggaagctccc tcgtgcgctc tcctgttccg accctgccgc ttaccggata    6300
cctgtccgcc tttctccctt cgggaagcgt ggcgctttct catagctcac gctgtaggta   6360
tctcagttcg gtgtaggtcg ttcgctccaa gctgggctgt gtgcacgaac cccccgttca   6420
gcccgaccgc tgcgccttat ccggtaacta tcgtcttgag tccaacccgg taagacacga   6480
cttatcgcca ctggcagcag ccactggtaa caggattagc agagcgaggt atgtaggcgg   6540
tgctacagag ttcttgaagt ggtggcctaa ctacggctac actagaagaa cagtatttgg   6600
tatctggct ctgctgaagc cagttacctc ggaaaaagag ttggtagctc ttgatccggc    6660
aaacaaacca ccgctggtag cggtggtttt tttgtttgca agcagcagat tacgcgcaga   6720
aaaaaaggat ctcaagaaga tcctttgatt ttctaccgaa gaaaggccca cccgtgaagg   6780
tgagccagtg agttgattgc agtccagtta cgctggagtc tgaggctcgt cctgaatgat   6840
atcaagcttg aattcgtt                                                 6858
```

SEQ ID NO: 20          moltype = DNA   length = 4051
FEATURE                Location/Qualifiers
source                 1..4051
                       mol_type = other DNA
                       organism = synthetic construct
SEQUENCE: 20

```
ggaagcggaa gagcgcccaa tacgcaaacc gcctctcccc gcgcgttggc cgattcatta    60
atgcaggggg atctcgatcc cgcgaaatta atacgactca ctatagagta gtgtactcca   120
cgcataaaac tttttatcgt tgagacatta ctactagagg atttgagtct ttgacttatt   180
cttttctttt caatggtgag caagggcgag gagctgttca ccggggtggt gcccatcctg   240
gtcgagctgg acggcgacgt aaacggccac aagttcagcg tgtccggcga gggcgagggc   300
gatgccacct acggcaagct gaccctgaag ttcatctgca ccaccggcaa gctgcccgtg   360
cccctggccca cctcgtgac cacccctgacc tacggcgtgc agtgcttcag ccgctacccc   420
gaccacatga agcagcacga cttcttcaag tccgccatgc ccgaaggcta cgtccaggag   480
cgcaccatct tcttcaagga cgacggcaac tacaagaccc gcgccgaggt gaagttcgag   540
ggcgacaccc tggtgaaccg catcgagctg aagggcatcg acttcaagga ggacggcaac   600
atcctggggc acaagctgga gtacaactac aacagccaca acgtctatat catggccgac   660
aagcagaaga acggcatcaa ggtgaacttc aagatccgcc acaacatcga ggacggcagc   720
gtgcagctcg ccgaccacta ccagcagaac accccccatcg cgacggcccc cgtgctgctg   780
cccgacaacc actacctgag cacccagtcc gccctgagca aagaccccaa cgagaagcgc   840
gatcacatgg tcctgctgga gttcgtgacc gccgccggga tcactctcgg catgacgag    900
ctgtacaagg gaagcggagc tactaacttc agcctgctga gcaggctgg agacgtggag    960
gagaaccctg gaccttggga gctagaattt gaagatgtcc ctactaacat cgggagtact   1020
tttgaccctg aatcaggata cattaacttt cagcgtaact acctgccagg ggttacgctt   1080
gaccaaattc gtatcttcta cattaaagga cgcgaaatca aaatagtct cgcaaaaga    1140
agtgaatggg aagttacgct taatcttggg ggctggaagg tgcctgtact caatacgaat   1200
ttccctggaa acaggagcaa tgcagtgcct gactacggtc ttaccttcca ccgcatcagc   1260
ggataccttg ccaggtactt acttggaaaa taccttgcag aaactgaacc agaaaagctc   1320
ataatgagaa caaaaatcat caaccctctt gctgagaaaa atggcatcac ctgggaaagt   1380
ggaccagtg tttatctctc attcttccct ggtcagtaga tgttccttgg aactttcaag   1440
ttctatccac ttgccattgg aatctacaaa gtgcagagga aagagatgga cccaaaattc   1500
ctggaaaaga caatgcgcca gaggtaccct ggccttgatg ctcagacatg acaacaact    1560
aagcttgatg aagtggagag agccctaaaa gtggtctcag ggcttggctg gagaaaaacc   1620
aatgtcgcca atgctgcaag ggaattcctg tctaagtttg gaatcagaat gtaaggattc   1680
agaaagagaa aataattcgg ccaaatttca ttatattaat tcgaccaaaa agggggtttt   1740
```

-continued

```
taccccaaac aatcaaagca gcattgcaga tgggtgggtg gttggggaca gtaactgact 1800
acaacattaa tttaacattt cactttattt gatattgttt aagtttaagg tggagcacac 1860
tactgggtcg gcatggcatc tccacctcct cgcggtccga cctgggcatc cgaaggagga 1920
cgtcgtccac tcgcatggct aagggagagc tcggatccgg ctgctaacaa agcccgaaag 1980
gaagctgagt tggctgctgc caccgctgag caataactag cataacccct tggggcctct 2040
aaacgggtct tgaggggttt tttgctgaaa ggaggaacta tatgacgaat tctctagata 2100
tcgctcaata ctgaccattt aaatcatacc tgacctccat agcagaaagt caaaagcctc 2160
cgaccggagg cttttgactt gatcggcacg taagaggttc caactttcac cataatgaaa 2220
taagatcact accgggcgta tttttttgagt tatcgagatt ttcaggagct atgagccata 2280
ttcaacggga aacgtcttgc tcgaggccgc gattaaattc caacatggat gctgatttat 2340
atgggtataa atgggctcgc gataatgtcg ggcaatcagg tgcgacaatc tatcgattgt 2400
atgggaagcc cgatgcgcca gagttgtttc tgaaacatgg caaaggtagc gttgccaatg 2460
atgttacaga tgagatggtc aggctaaact ggctgacgga atttatgcct cttccgacca 2520
tcaagcattt tatccgtact cctgatgatg catggttact caccactgcg atcccaggga 2580
aaacagcatt ccaggtatta gaagaatatc ctgattcagg tgaaaatatt gttgatgcgc 2640
tggcagtgtt cctgcgccgg ttgcattcga ttcctgtttg taattgtcct tttaacggcg 2700
atcgcgtatt tcgtctcgct caggcgcaat cacgaatgaa taacggtttg gttggtgcga 2760
gtgattttga tgacgagcgt aatggctggc ctgttgaaca agtctggaaa gaaatgcata 2820
agcttttgcc attctcaccg gattcagtcg tcactcatgg tgatttctca cttgataacc 2880
ttatttttga cgaggggaaa ttaataggtt gtattgatgt tggacgagtc ggaatcgcag 2940
accgatacca ggatcttgcc atcctatgga actgcctcgg tgagttttct ccttcattac 3000
agaaacggct ttttcaaaaa tatggtattg ataatcctga tatgaataaa ttgcagtttc 3060
acttgatgct cgatgagttt ttctaaatga ccaaacagga aaaaaccgcc cttaacatgg 3120
cccgctttat cagaagccag acattaacgc ttctggagaa actcaacgag ctggacgcgg 3180
atgaacaggc agacatctgt gaatcgcttc acgaccacgc tgatgagctt taccgcagct 3240
gcctcgcgcg tttcggtgat gacggtgaaa acctctgatg agggcccaaa tgtaatcacc 3300
tggctcacct tcgggtgggc ctttctgcgt tgctggcgtt tttccatagg ctccgccccc 3360
ctgacgagca tcacaaaaat cgatgctcaa gtcagaggtg gcgaaacccg acaggactat 3420
aaagatacca ggcgtttccc cctggaagct ccctcgtgcg ctctcctgtt ccgaccctgc 3480
cgcttaccgg atacctgtcc gcctttctcc cttcgggaag cgtggcgctt tctcatagct 3540
cacgctgtag gtatctcagt tcggtgtagg tcgttcgctc caagctgggc tgtgtgcacg 3600
aaccccccgt tcagcccgac cgctgcgcct tatccggtaa ctatcgtctt gagtccaacc 3660
cggtaagaca cgacttatcg ccactggcag cagccactgg taacaggatt agcagagcga 3720
ggtatgtagg cggtgctaca gagttcttga agtggtggcc taactacggc tacactagaa 3780
gaacagtatt tggtatctgc gctctgctga agccagttac ctcggaaaaa gagttggtag 3840
ctcttgatcc ggcaaacaaa ccaccgctgg tagcggtggt ttttttgttt gcaagcagca 3900
gattacgcgc agaaaaaaag gatctcaaga agatcctttg attttctacc gaagaaaggc 3960
ccaccgtga aggtgagcca gtgagttgat tgcagtccag ttacgctgga gtctgaggct 4020
cgtcctgaat gatatcaagc ttgaattcgt t                            4051
```